(12) United States Patent
Sims et al.

(10) Patent No.: US 7,285,634 B2
(45) Date of Patent: Oct. 23, 2007

(54) IL-1 RECEPTOR ACCESSORY PROTEIN

(75) Inventors: John E Sims, Seattle, WA (US); Dirk E Smith, Bainbridge Island, WA (US)

(73) Assignee: Immunex Corporation, Thousand Oaks, CA (US)

( * ) Notice: Subject to any disclaimer, the term of this patent is extended or adjusted under 35 U.S.C. 154(b) by 0 days.

(21) Appl. No.: 11/387,672

(22) Filed: Mar. 23, 2006

(65) Prior Publication Data

US 2006/0166256 A1 Jul. 27, 2006

Related U.S. Application Data

(62) Division of application No. 10/061,727, filed on Oct. 26, 2001, now Pat. No. 7,049,095.

(60) Provisional application No. 60/244,831, filed on Oct. 31, 2000.

(51) Int. Cl.
*C07K 14/435* (2006.01)
*C07K 7/00* (2006.01)

(52) U.S. Cl. ........................ 530/350; 530/300

(58) Field of Classification Search ............. None
See application file for complete search history.

(56) References Cited

FOREIGN PATENT DOCUMENTS

WO    WO97 23067    8/1996

OTHER PUBLICATIONS

Cao, Z., GenBank, Accession No. AR166115, 2001.
Greenfeder et al., "Molecular cloning a characterization of a second subunit of the interleukin 1 receptor complex", *J. Biol. Chem.* 270(23):13757-13765, 1995.
Huang et al., "Recuitment of IRAK to the interleukin 1 receptor complex requires interleukin 1 receptor accessory protein", *Proc. Natl. Acad. Sci. USA* 94:12829-12832, 1997.
Huang et al., GenBank, Accession No. AF029213, Sep. 30, 1999.
Jensen, et al., "IL-1 signaling cascade in liver cells and the involvement of a soluble form of the IL-1 receptor accessory proteins," *J. of Immunol.* 164(10):5277-5286, 2000.
Parnet et al., "IL-1Rrp is a novel receptor-like molecule similar to the type I interleukin-1 receptor and its homologues T1/ST2 and IL-1R AcP," *J. of Biol. Chem.* 271(8):3967-3970, 1996.
Sims et al., "A new nomenclature for IL-1-family genes," *Trends in Immunol.* 22(10):536-537, 2001.

*Primary Examiner*—Ruixiang Li
(74) *Attorney, Agent, or Firm*—Patricia Anne Perkins

(57) ABSTRACT

DNA encoding IL-1R AcP splice variant polypeptides, the polypeptides and methods for using the encoded polypeptides are disclosed.

2 Claims, 1 Drawing Sheet

SEQUENCE LISTING

```
<160> NUMBER OF SEQ ID NOS: 4

<210> SEQ ID NO 1
<211> LENGTH: 2064
<212> TYPE: DNA
<213> ORGANISM: Homo sapiens
<220> FEATURE:
<221> NAME/KEY: CDS
<222> LOCATION: (1)..(2064)
<223> OTHER INFORMATION:
<220> FEATURE:
<221> NAME/KEY: misc_feature
<222> LOCATION: (1792)..(1792)
<223> OTHER INFORMATION: "n" = a or c. Xaa at amino acid position 598 is
      Thr or Pro.

<400> SEQUENCE: 1 atg aca ctt ctg tgg tgt gta gtg agt ctc tac ttt tat gga atc ctg        48
Met Thr Leu Leu Trp Cys Val Val Ser Leu Tyr Phe Tyr Gly Ile Leu
1               5                   10                  15 caa agt gat gcc tca gaa cgc tgc gat gac tgg gga cta gac acc atg        96
Gln Ser Asp Ala Ser Glu Arg Cys Asp Asp Trp Gly Leu Asp Thr Met
            20                  25                  30 agg caa atc caa gtg ttt gaa gat gag cca gct cgc atc aag tgc cca       144
Arg Gln Ile Gln Val Phe Glu Asp Glu Pro Ala Arg Ile Lys Cys Pro
        35                  40                  45 ctc ttt gaa cac ttc ttg aaa ttc aac tac agc aca gcc cat tca gct       192
Leu Phe Glu His Phe Leu Lys Phe Asn Tyr Ser Thr Ala His Ser Ala
    50                  55                  60 ggc ctt act ctg atc tgg tat tgg act agg cag gac cgg gac ctt gag       240
Gly Leu Thr Leu Ile Trp Tyr Trp Thr Arg Gln Asp Arg Asp Leu Glu
65                  70                  75                  80 gag cca att aac ttc cgc ctc ccc gag aac cgc att agt aag gag aaa       288
Glu Pro Ile Asn Phe Arg Leu Pro Glu Asn Arg Ile Ser Lys Glu Lys
                85                  90                  95 gat gtg ctg tgg ttc cgg ccc act ctc ctc aat gac act ggc aac tat       336
Asp Val Leu Trp Phe Arg Pro Thr Leu Leu Asn Asp Thr Gly Asn Tyr
            100                 105                 110 acc tgc atg tta agg aac act aca tat tgc agc aaa gtt gca ttt ccc       384
Thr Cys Met Leu Arg Asn Thr Thr Tyr Cys Ser Lys Val Ala Phe Pro
        115                 120                 125 ttg gaa gtt gtt caa aaa gac agc tgt ttc aat tcc ccc atg aaa ctc       432
```

-continued

| | | |
|---|---|---|
| Leu Glu Val Val Gln Lys Asp Ser Cys Phe Asn Ser Pro Met Lys Leu<br>130                 135                 140 | | |
| cca gtg cat aaa ctg tat ata gaa tat ggc att cag agg atc act tgt<br>Pro Val His Lys Leu Tyr Ile Glu Tyr Gly Ile Gln Arg Ile Thr Cys<br>145                 150                 155                 160 | | 480 |
| cca aat gta gat gga tat ttt cct tcc agt gtc aaa ccg act atc act<br>Pro Asn Val Asp Gly Tyr Phe Pro Ser Ser Val Lys Pro Thr Ile Thr<br>                165                 170                 175 | | 528 |
| tgg tat atg ggc tgt tat aaa ata cag aat ttt aat aat gta ata ccc<br>Trp Tyr Met Gly Cys Tyr Lys Ile Gln Asn Phe Asn Asn Val Ile Pro<br>            180                 185                 190 | | 576 |
| gaa ggt atg aac ttg agt ttc ctc att gcc tta att tca aat aat gga<br>Glu Gly Met Asn Leu Ser Phe Leu Ile Ala Leu Ile Ser Asn Asn Gly<br>        195                 200                 205 | | 624 |
| aat tac aca tgt gtt gtt aca tat cca gaa aat gga cgt acg ttt cat<br>Asn Tyr Thr Cys Val Val Thr Tyr Pro Glu Asn Gly Arg Thr Phe His<br>    210                 215                 220 | | 672 |
| ctc acc agg act ctg act gta aag gta gta ggc tct cca aaa aat gca<br>Leu Thr Arg Thr Leu Thr Val Lys Val Val Gly Ser Pro Lys Asn Ala<br>225                 230                 235                 240 | | 720 |
| gtg ccc cct gtg atc cat tca cct aat gat cat gtg gtc tat gag aaa<br>Val Pro Pro Val Ile His Ser Pro Asn Asp His Val Val Tyr Glu Lys<br>                245                 250                 255 | | 768 |
| gaa cca gga gag gag cta ctc att ccc tgt acg gtc tat ttt agt ttt<br>Glu Pro Gly Glu Glu Leu Leu Ile Pro Cys Thr Val Tyr Phe Ser Phe<br>            260                 265                 270 | | 816 |
| ctg atg gat tct cgc aat gag gtt tgg tgg acc att gat gga aaa aaa<br>Leu Met Asp Ser Arg Asn Glu Val Trp Trp Thr Ile Asp Gly Lys Lys<br>        275                 280                 285 | | 864 |
| cct gat gac atc act att gat gtc acc att aac gaa agt ata agt cat<br>Pro Asp Asp Ile Thr Ile Asp Val Thr Ile Asn Glu Ser Ile Ser His<br>    290                 295                 300 | | 912 |
| agt aga aca gaa gat gaa aca aga act cag att ttg agc atc aag aaa<br>Ser Arg Thr Glu Asp Glu Thr Arg Thr Gln Ile Leu Ser Ile Lys Lys<br>305                 310                 315                 320 | | 960 |
| gtt acc tct gag gat ctc aag cgc agc tat gtc tgt cat gct aga agt<br>Val Thr Ser Glu Asp Leu Lys Arg Ser Tyr Val Cys His Ala Arg Ser<br>                325                 330                 335 | | 1008 |
| gcc aaa ggc gaa gtt gcc aaa gca gcc aag gtg aag cag aaa gtg cca<br>Ala Lys Gly Glu Val Ala Lys Ala Ala Lys Val Lys Gln Lys Val Pro<br>            340                 345                 350 | | 1056 |
| gct cca aga tac aca gtg gaa ctg gct tgt ggt ttt gga gcc aca gtc<br>Ala Pro Arg Tyr Thr Val Glu Leu Ala Cys Gly Phe Gly Ala Thr Val<br>        355                 360                 365 | | 1104 |
| ctg cta gtg gtg att ctc att gtt gtt tac cat gtt tac tgg cta gag<br>Leu Leu Val Val Ile Leu Ile Val Val Tyr His Val Tyr Trp Leu Glu<br>    370                 375                 380 | | 1152 |
| atg gtc cta ttt tac cgg gct cat ttt gga aca gat gaa acc att tta<br>Met Val Leu Phe Tyr Arg Ala His Phe Gly Thr Asp Glu Thr Ile Leu<br>385                 390                 395                 400 | | 1200 |
| gat gga aaa gag tat gat att tat gta tcc tat gca agg aat gcg gaa<br>Asp Gly Lys Glu Tyr Asp Ile Tyr Val Ser Tyr Ala Arg Asn Ala Glu<br>                405                 410                 415 | | 1248 |
| gaa gaa gaa ttt gta tta ctg acc ctc cgt gga gtt tgt gag aat gaa<br>Glu Glu Glu Phe Val Leu Leu Thr Leu Arg Gly Val Leu Glu Asn Glu<br>            420                 425                 430 | | 1296 |
| ttt gga tac aag ctg tgc atc ttt gac cga gac agt ctg cct ggg gga<br>Phe Gly Tyr Lys Leu Cys Ile Phe Asp Arg Asp Ser Leu Pro Gly Gly<br>        435                 440                 445 | | 1344 |

```
aat aca gtg gaa gca gtt ttt gat ttc att cag aga agc aga agg atg    1392
Asn Thr Val Glu Ala Val Phe Asp Phe Ile Gln Arg Ser Arg Arg Met
    450                 455                 460 att gtt gtt ctg agc cct gac tat gtg aca gaa aag agc atc agc atg    1440
Ile Val Val Leu Ser Pro Asp Tyr Val Thr Glu Lys Ser Ile Ser Met
465                 470                 475                 480 ctg gag ttt aaa ctg ggt gtc atg tgc cag aac tcc att gcc acc aag    1488
Leu Glu Phe Lys Leu Gly Val Met Cys Gln Asn Ser Ile Ala Thr Lys
                485                 490                 495 ctc att gtg gtt gag tac cgt ccc ctt gag cac ccg cac cca ggc att    1536
Leu Ile Val Val Glu Tyr Arg Pro Leu Glu His Pro His Pro Gly Ile
            500                 505                 510 ctt cag ctc aaa gag tct gtg tct ttt gtg agc tgg aag gga gaa aag    1584
Leu Gln Leu Lys Glu Ser Val Ser Phe Val Ser Trp Lys Gly Glu Lys
        515                 520                 525 tcc aaa cat tct ggc tct aaa ttc tgg aaa gct ttg cgg ttg gct ctt    1632
Ser Lys His Ser Gly Ser Lys Phe Trp Lys Ala Leu Arg Leu Ala Leu
    530                 535                 540 ccc ctg aga agt ctg agt gcc agt tct ggc tgg aat gag agc tgc tct    1680
Pro Leu Arg Ser Leu Ser Ala Ser Ser Gly Trp Asn Glu Ser Cys Ser
545                 550                 555                 560 tcc cag tct gac atc agt ctg gat cac gtt caa agg agg aga agt cgt    1728
Ser Gln Ser Asp Ile Ser Leu Asp His Val Gln Arg Arg Arg Ser Arg
                565                 570                 575 ttg aaa gag ccc cca gaa ctt cag agc tca gag agg gct gca ggt agc    1776
Leu Lys Glu Pro Pro Glu Leu Gln Ser Ser Glu Arg Ala Ala Gly Ser
            580                 585                 590 cct cca gcc cca ggc nca atg tcc aag cac cga ggg aag tcc tcc gcc    1824
Pro Pro Ala Pro Gly Xaa Met Ser Lys His Arg Gly Lys Ser Ser Ala
        595                 600                 605 acc tgc cgc tgt tgt gtc acc tac tgt gaa gga gag aat cac ctt agg    1872
Thr Cys Arg Cys Cys Val Thr Tyr Cys Glu Gly Glu Asn His Leu Arg
    610                 615                 620 aac aag agc cgg gca gag att cat aac cag ccc cag tgg gag aca cac    1920
Asn Lys Ser Arg Ala Glu Ile His Asn Gln Pro Gln Trp Glu Thr His
625                 630                 635                 640 ctc tgt aag cct gtt ccc caa gag tca gaa act caa tgg ata caa aat    1968
Leu Cys Lys Pro Val Pro Gln Glu Ser Glu Thr Gln Trp Ile Gln Asn
                645                 650                 655 ggc acc aga ttg gaa ccc cct gct ccc cag atc tca gcc ctt gct ctt    2016
Gly Thr Arg Leu Glu Pro Pro Ala Pro Gln Ile Ser Ala Leu Ala Leu
            660                 665                 670 cat cat ttc acg gac tta tcc aat aac aac gac ttt tat atc cta taa   2064
His His Phe Thr Asp Leu Ser Asn Asn Asn Asp Phe Tyr Ile Leu
        675                 680                 685

<210> SEQ ID NO 2
<211> LENGTH: 687
<212> TYPE: PRT
<213> ORGANISM: Homo sapiens
<220> FEATURE:
<221> NAME/KEY: misc_feature
<222> LOCATION: (598)..(598)
<223> OTHER INFORMATION: The 'Xaa' at location 598 stands for Thr or
      Pro.

<400> SEQUENCE: 2

Met Thr Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30
```

-continued

```
Arg Gln Ile Gln Val Phe Glu Asp Glu Pro Ala Arg Ile Lys Cys Pro
         35                  40                  45
Leu Phe Glu His Phe Leu Lys Phe Asn Tyr Ser Thr Ala His Ser Ala
 50                  55                  60
Gly Leu Thr Leu Ile Trp Tyr Trp Thr Arg Gln Asp Arg Asp Leu Glu
 65                  70                  75                  80
Glu Pro Ile Asn Phe Arg Leu Pro Glu Asn Arg Ile Ser Lys Glu Lys
                 85                  90                  95
Asp Val Leu Trp Phe Arg Pro Thr Leu Leu Asn Asp Thr Gly Asn Tyr
                100                 105                 110
Thr Cys Met Leu Arg Asn Thr Thr Tyr Cys Ser Lys Val Ala Phe Pro
            115                 120                 125
Leu Glu Val Val Gln Lys Asp Ser Cys Phe Asn Ser Pro Met Lys Leu
    130                 135                 140
Pro Val His Lys Leu Tyr Ile Glu Tyr Gly Ile Gln Arg Ile Thr Cys
145                 150                 155                 160
Pro Asn Val Asp Gly Tyr Phe Pro Ser Ser Val Lys Pro Thr Ile Thr
                165                 170                 175
Trp Tyr Met Gly Cys Tyr Lys Ile Gln Asn Phe Asn Asn Val Ile Pro
            180                 185                 190
Glu Gly Met Asn Leu Ser Phe Leu Ile Ala Leu Ile Ser Asn Asn Gly
    195                 200                 205
Asn Tyr Thr Cys Val Val Thr Tyr Pro Glu Asn Gly Arg Thr Phe His
    210                 215                 220
Leu Thr Arg Thr Leu Thr Val Lys Val Val Gly Ser Pro Lys Asn Ala
225                 230                 235                 240
Val Pro Pro Val Ile His Ser Pro Asn Asp His Val Val Tyr Glu Lys
                245                 250                 255
Glu Pro Gly Glu Glu Leu Leu Ile Pro Cys Thr Val Tyr Phe Ser Phe
            260                 265                 270
Leu Met Asp Ser Arg Asn Glu Val Trp Trp Thr Ile Asp Gly Lys Lys
    275                 280                 285
Pro Asp Asp Ile Thr Ile Asp Val Thr Ile Asn Glu Ser Ile Ser His
    290                 295                 300
Ser Arg Thr Glu Asp Glu Thr Arg Thr Gln Ile Leu Ser Ile Lys Lys
305                 310                 315                 320
Val Thr Ser Glu Asp Leu Lys Arg Ser Tyr Val Cys His Ala Arg Ser
                325                 330                 335
Ala Lys Gly Glu Val Ala Lys Ala Ala Lys Val Lys Gln Lys Val Pro
            340                 345                 350
Ala Pro Arg Tyr Thr Val Glu Leu Ala Cys Gly Phe Gly Ala Thr Val
    355                 360                 365
Leu Leu Val Val Ile Leu Ile Val Val Tyr His Val Tyr Trp Leu Glu
    370                 375                 380
Met Val Leu Phe Tyr Arg Ala His Phe Gly Thr Asp Glu Thr Ile Leu
385                 390                 395                 400
Asp Gly Lys Glu Tyr Asp Ile Tyr Val Ser Tyr Ala Arg Asn Ala Glu
                405                 410                 415
Glu Glu Glu Phe Val Leu Leu Thr Leu Arg Gly Val Leu Glu Asn Glu
            420                 425                 430
Phe Gly Tyr Lys Leu Cys Ile Phe Asp Arg Asp Ser Leu Pro Gly Gly
    435                 440                 445
Asn Thr Val Glu Ala Val Phe Asp Phe Ile Gln Arg Ser Arg Arg Met
```

-continued

```
                450                 455                 460
Ile Val Val Leu Ser Pro Asp Tyr Val Thr Glu Lys Ser Ile Ser Met
465                 470                 475                 480

Leu Glu Phe Lys Leu Gly Val Met Cys Gln Asn Ser Ile Ala Thr Lys
                485                 490                 495

Leu Ile Val Val Glu Tyr Arg Pro Leu Glu His Pro His Pro Gly Ile
            500                 505                 510

Leu Gln Leu Lys Glu Ser Val Ser Phe Val Ser Trp Lys Gly Glu Lys
            515                 520                 525

Ser Lys His Ser Gly Ser Lys Phe Trp Lys Ala Leu Arg Leu Ala Leu
            530                 535                 540

Pro Leu Arg Ser Leu Ser Ala Ser Ser Gly Trp Asn Glu Ser Cys Ser
545                 550                 555                 560

Ser Gln Ser Asp Ile Ser Leu Asp His Val Gln Arg Arg Ser Arg
                565                 570                 575

Leu Lys Glu Pro Pro Glu Leu Gln Ser Glu Arg Ala Ala Gly Ser
            580                 585                 590

Pro Pro Ala Pro Gly Xaa Met Ser Lys His Arg Gly Lys Ser Ser Ala
            595                 600                 605

Thr Cys Arg Cys Cys Val Thr Tyr Cys Glu Gly Glu Asn His Leu Arg
610                 615                 620

Asn Lys Ser Arg Ala Glu Ile His Asn Gln Pro Gln Trp Glu Thr His
625                 630                 635                 640

Leu Cys Lys Pro Val Pro Gln Glu Ser Glu Thr Gln Trp Ile Gln Asn
                645                 650                 655

Gly Thr Arg Leu Glu Pro Pro Ala Pro Gln Ile Ser Ala Leu Ala Leu
            660                 665                 670

His His Phe Thr Asp Leu Ser Asn Asn Asn Asp Phe Tyr Ile Leu
            675                 680                 685
```

<210> SEQ ID NO 3
<211> LENGTH: 2058
<212> TYPE: DNA
<213> ORGANISM: Mus musculus
<220> FEATURE:
<221> NAME/KEY: CDS
<222> LOCATION: (1)..(2058)
<223> OTHER INFORMATION:

<400> SEQUENCE: 3

```
atg gga ctt ctg tgg tat ttg atg agt ctg tcc ttc tat ggg atc ctg    48
Met Gly Leu Leu Trp Tyr Leu Met Ser Leu Ser Phe Tyr Gly Ile Leu
1               5                   10                  15 cag agt cat gct tcg gag cgc tgt gat gac tgg gga cta gat acc atg    96
Gln Ser His Ala Ser Glu Arg Cys Asp Asp Trp Gly Leu Asp Thr Met
                20                  25                  30 cga caa atc caa gtg ttt gaa gat gag ccg gct cga atc aag tgc ccc    144
Arg Gln Ile Gln Val Phe Glu Asp Glu Pro Ala Arg Ile Lys Cys Pro
            35                  40                  45 ctc ttt gaa cac ttc ctg aag tac aac tac agc act gcc cat tcc tct    192
Leu Phe Glu His Phe Leu Lys Tyr Asn Tyr Ser Thr Ala His Ser Ser
        50                  55                  60 ggc ctt acc ctg atc tgg tac tgg acc agg caa gac cgg gac ctg gag    240
Gly Leu Thr Leu Ile Trp Tyr Trp Thr Arg Gln Asp Arg Asp Leu Glu
65                  70                  75                  80 gag ccc att aac ttc cgc ctc cca gag aat cgc atc agt aag gag aaa    288
Glu Pro Ile Asn Phe Arg Leu Pro Glu Asn Arg Ile Ser Lys Glu Lys
                85                  90                  95
```

```
gat gtg ctc tgg ttc cgg ccc acc ctc ctc aat gac acg ggc aat tac      336
Asp Val Leu Trp Phe Arg Pro Thr Leu Leu Asn Asp Thr Gly Asn Tyr
            100                 105                 110 acc tgc atg ttg agg aac aca act tac tgc agc aaa gtt gca ttt ccc      384
Thr Cys Met Leu Arg Asn Thr Thr Tyr Cys Ser Lys Val Ala Phe Pro
        115                 120                 125 ctg gaa gtt gtt cag aag gac agc tgt ttc aat tct gcc atg aga ttc      432
Leu Glu Val Val Gln Lys Asp Ser Cys Phe Asn Ser Ala Met Arg Phe
130                 135                 140 cca gtg cac aag atg tat att gaa cat ggc att cat aag atc aca tgt      480
Pro Val His Lys Met Tyr Ile Glu His Gly Ile His Lys Ile Thr Cys
145                 150                 155                 160 cca aat gta gac gga tac ttt cct tcc agt gtc aaa cca tcg gtc act      528
Pro Asn Val Asp Gly Tyr Phe Pro Ser Ser Val Lys Pro Ser Val Thr
            165                 170                 175 tgg tat aag ggt tgt act gaa ata gtg gac ttt cat aat gta cta ccc      576
Trp Tyr Lys Gly Cys Thr Glu Ile Val Asp Phe His Asn Val Leu Pro
        180                 185                 190 gag ggc atg aac ttg agc ttt ttc atc ccc ttg gtt tca aat aac gga      624
Glu Gly Met Asn Leu Ser Phe Phe Ile Pro Leu Val Ser Asn Asn Gly
    195                 200                 205 aat tac aca tgt gtg gtt aca tat cct gaa aac gga cgt ctc ttt cac      672
Asn Tyr Thr Cys Val Val Thr Tyr Pro Glu Asn Gly Arg Leu Phe His
210                 215                 220 ctc acc agg act gtg act gta aag gtg gtg ggc tca cca aag gat gca      720
Leu Thr Arg Thr Val Thr Val Lys Val Val Gly Ser Pro Lys Asp Ala
225                 230                 235                 240 ttg cca ccc cag atc tat tct cca aat gac cgt gtt gtc tat gag aaa      768
Leu Pro Pro Gln Ile Tyr Ser Pro Asn Asp Arg Val Val Tyr Glu Lys
            245                 250                 255 gaa cca gga gag gaa ctg gtt att ccc tgc aaa gtc tat ttc agt ttc      816
Glu Pro Gly Glu Glu Leu Val Ile Pro Cys Lys Val Tyr Phe Ser Phe
        260                 265                 270 att atg gac tcc cac aat gag gtc tgg tgg acc att gat gga aag aag      864
Ile Met Asp Ser His Asn Glu Val Trp Trp Thr Ile Asp Gly Lys Lys
    275                 280                 285 cct gat gac gtc aca gtc gac atc act att aat gaa agt gta agt tat      912
Pro Asp Asp Val Thr Val Asp Ile Thr Ile Asn Glu Ser Val Ser Tyr
290                 295                 300 tct tca acg gaa gat gaa aca agg act cag att ttg agc atc aag aaa      960
Ser Ser Thr Glu Asp Glu Thr Arg Thr Gln Ile Leu Ser Ile Lys Lys
305                 310                 315                 320 gtc acc ccg gag gat ctc agg cgc aac tat gtc tgt cat gct cga aat      1008
Val Thr Pro Glu Asp Leu Arg Arg Asn Tyr Val Cys His Ala Arg Asn
            325                 330                 335 acc aaa ggg gaa gct gag cag gct gcc aag gtg aaa cag aaa gtc ata      1056
Thr Lys Gly Glu Ala Glu Gln Ala Ala Lys Val Lys Gln Lys Val Ile
        340                 345                 350 cca cca agg tac aca gta gaa ctc gcc tgt ggt ttt gga gcc acg gtc      1104
Pro Pro Arg Tyr Thr Val Glu Leu Ala Cys Gly Phe Gly Ala Thr Val
    355                 360                 365 ttt ctg gta gtg gtt ctc att gtg gtt tac cat gtt tac tgg ctg gag      1152
Phe Leu Val Val Val Leu Ile Val Val Tyr His Val Tyr Trp Leu Glu
370                 375                 380 atg gtc ctc ttt tac cga gct cac ttt gga aca gat gaa aca att ctt      1200
Met Val Leu Phe Tyr Arg Ala His Phe Gly Thr Asp Glu Thr Ile Leu
385                 390                 395                 400 gat gga aag gag tat gat att tat gtt tcc tat gca aga aat gtg gaa      1248
Asp Gly Lys Glu Tyr Asp Ile Tyr Val Ser Tyr Ala Arg Asn Val Glu
```

-continued

```
                         405                 410                 415
gaa gag gaa ttt gtg ctg ctg acg ctg cgt gga gtt ttg gag aat gag      1296
Glu Glu Glu Phe Val Leu Leu Thr Leu Arg Gly Val Leu Glu Asn Glu
                420                 425                 430 ttt gga tac aag ctg tgc atc ttc gac aga gac agc ctg cct ggg gga      1344
Phe Gly Tyr Lys Leu Cys Ile Phe Asp Arg Asp Ser Leu Pro Gly Gly
            435                 440                 445 aat acc gtg gaa gca gtt ttt gat ttc att cag agg agc cga agg atg      1392
Asn Thr Val Glu Ala Val Phe Asp Phe Ile Gln Arg Ser Arg Arg Met
        450                 455                 460 att gtt gtc ctg agc cct gac tat gtg aca gaa aag agc atc agc atg      1440
Ile Val Val Leu Ser Pro Asp Tyr Val Thr Glu Lys Ser Ile Ser Met
465                 470                 475                 480 ctg gag ttt aag ctg ggt gtc atg tgc cag aac tcc att gcc act aag      1488
Leu Glu Phe Lys Leu Gly Val Met Cys Gln Asn Ser Ile Ala Thr Lys
                485                 490                 495 ctc att gtg gtg gag tac cgt ccg ctt gag caa ccc cat cca ggc atc      1536
Leu Ile Val Val Glu Tyr Arg Pro Leu Glu Gln Pro His Pro Gly Ile
            500                 505                 510 atg cag ctg aag gag tct gtg tct ttt gta agc tgg aag gga gaa aag      1584
Met Gln Leu Lys Glu Ser Val Ser Phe Val Ser Trp Lys Gly Glu Lys
        515                 520                 525 tcc aaa cat tct ggc tcc aag ttc tgg aag gcc ttg cgt ttg gct ctt      1632
Ser Lys His Ser Gly Ser Lys Phe Trp Lys Ala Leu Arg Leu Ala Leu
    530                 535                 540 ccc ctg aga agt ctg agc gcc agc tcc ggc tgg aat gag agc tgt tct      1680
Pro Leu Arg Ser Leu Ser Ala Ser Ser Gly Trp Asn Glu Ser Cys Ser
545                 550                 555                 560 tct cag tct gac atc agt ctg gat cat gtt cag agg aga agt cgt ttg      1728
Ser Gln Ser Asp Ile Ser Leu Asp His Val Gln Arg Arg Ser Arg Leu
                565                 570                 575 aaa gag ccc cca gaa ctc cga agc tca gag agg gtg tct gga gca gag      1776
Lys Glu Pro Pro Glu Leu Arg Ser Ser Glu Arg Val Ser Gly Ala Glu
            580                 585                 590 cca gcc ccg ggc acg atg tcc aag cac cga ggg aaa ccc tca gca gcc      1824
Pro Ala Pro Gly Thr Met Ser Lys His Arg Gly Lys Pro Ser Ala Ala
        595                 600                 605 tgt cgc tgc tgt gtc acc tac tgt gaa gga gaa agt cac ctc agg agc      1872
Cys Arg Cys Cys Val Thr Tyr Cys Glu Gly Glu Ser His Leu Arg Ser
    610                 615                 620 aag agc cgg gca gag atg cac acg cat ccc cag tgg gaa aca cac ctc      1920
Lys Ser Arg Ala Glu Met His Thr His Pro Gln Trp Glu Thr His Leu
625                 630                 635                 640 tgt aag cct cct ctc caa gag tct gaa agt cag tgg ata caa aat ggc      1968
Cys Lys Pro Pro Leu Gln Glu Ser Glu Ser Gln Trp Ile Gln Asn Gly
                645                 650                 655 acc cga ccc gaa ccc gct ccc cag atc tca gct ctt gca ctc cgc cac      2016
Thr Arg Pro Glu Pro Ala Pro Gln Ile Ser Ala Leu Ala Leu Arg His
            660                 665                 670 ttt aca gat tta tcc aat aac aat gac ttt tat atc cta taa              2058
Phe Thr Asp Leu Ser Asn Asn Asn Asp Phe Tyr Ile Leu
        675                 680                 685
```

<210> SEQ ID NO 4
<211> LENGTH: 685
<212> TYPE: PRT
<213> ORGANISM: Mus musculus

<400> SEQUENCE: 4

Met Gly Leu Leu Trp Tyr Leu Met Ser Leu Ser Phe Tyr Gly Ile Leu

```
1               5                   10                  15
Gln Ser His Ala Ser Glu Arg Cys Asp Asp Trp Gly Leu Asp Thr Met
                20                  25                  30
Arg Gln Ile Gln Val Phe Glu Asp Glu Pro Ala Arg Ile Lys Cys Pro
                35                  40                  45
Leu Phe Glu His Phe Leu Lys Tyr Asn Tyr Ser Thr Ala His Ser Ser
                50                  55                  60
Gly Leu Thr Leu Ile Trp Tyr Trp Thr Arg Gln Asp Arg Asp Leu Glu
 65                 70                  75                  80
Glu Pro Ile Asn Phe Arg Leu Pro Glu Asn Arg Ile Ser Lys Glu Lys
                85                  90                  95
Asp Val Leu Trp Phe Arg Pro Thr Leu Leu Asn Asp Thr Gly Asn Tyr
                100                 105                 110
Thr Cys Met Leu Arg Asn Thr Thr Tyr Cys Ser Lys Val Ala Phe Pro
                115                 120                 125
Leu Glu Val Val Gln Lys Asp Ser Cys Phe Asn Ser Ala Met Arg Phe
                130                 135                 140
Pro Val His Lys Met Tyr Ile Glu His Gly Ile His Lys Ile Thr Cys
145                 150                 155                 160
Pro Asn Val Asp Gly Tyr Phe Pro Ser Ser Val Lys Pro Ser Val Thr
                165                 170                 175
Trp Tyr Lys Gly Cys Thr Glu Ile Val Asp Phe His Asn Val Leu Pro
                180                 185                 190
Glu Gly Met Asn Leu Ser Phe Phe Ile Pro Leu Val Ser Asn Asn Gly
                195                 200                 205
Asn Tyr Thr Cys Val Val Thr Tyr Pro Glu Asn Gly Arg Leu Phe His
                210                 215                 220
Leu Thr Arg Thr Val Thr Val Lys Val Gly Ser Pro Lys Asp Ala
225                 230                 235                 240
Leu Pro Pro Gln Ile Tyr Ser Pro Asn Asp Arg Val Val Tyr Glu Lys
                245                 250                 255
Glu Pro Gly Glu Glu Leu Val Ile Pro Cys Lys Val Tyr Phe Ser Phe
                260                 265                 270
Ile Met Asp Ser His Asn Glu Val Trp Trp Thr Ile Asp Gly Lys Lys
                275                 280                 285
Pro Asp Asp Val Thr Val Asp Ile Thr Ile Asn Glu Ser Val Ser Tyr
                290                 295                 300
Ser Ser Thr Glu Asp Glu Thr Arg Thr Gln Ile Leu Ser Ile Lys Lys
305                 310                 315                 320
Val Thr Pro Glu Asp Leu Arg Arg Asn Tyr Val Cys His Ala Arg Asn
                325                 330                 335
Thr Lys Gly Glu Ala Glu Gln Ala Ala Lys Val Lys Gln Lys Val Ile
                340                 345                 350
Pro Pro Arg Tyr Thr Val Glu Leu Ala Cys Gly Phe Gly Ala Thr Val
                355                 360                 365
Phe Leu Val Val Val Leu Ile Val Val Tyr His Val Tyr Trp Leu Glu
                370                 375                 380
Met Val Leu Phe Tyr Arg Ala His Phe Gly Thr Asp Glu Thr Ile Leu
385                 390                 395                 400
Asp Gly Lys Glu Tyr Asp Ile Tyr Val Ser Tyr Ala Arg Asn Val Glu
                405                 410                 415
Glu Glu Glu Phe Val Leu Leu Thr Leu Arg Gly Val Leu Glu Asn Glu
                420                 425                 430
```

```
Phe Gly Tyr Lys Leu Cys Ile Phe Asp Arg Asp Ser Leu Pro Gly Gly
        435                 440                 445

Asn Thr Val Glu Ala Val Phe Asp Phe Ile Gln Arg Ser Arg Arg Met
    450                 455                 460

Ile Val Val Leu Ser Pro Asp Tyr Val Thr Glu Lys Ser Ile Ser Met
465                 470                 475                 480

Leu Glu Phe Lys Leu Gly Val Met Cys Gln Asn Ser Ile Ala Thr Lys
                485                 490                 495

Leu Ile Val Val Glu Tyr Arg Pro Leu Glu Gln Pro His Pro Gly Ile
                500                 505                 510

Met Gln Leu Lys Glu Ser Val Ser Phe Val Ser Trp Lys Gly Glu Lys
        515                 520                 525

Ser Lys His Ser Gly Ser Lys Phe Trp Lys Ala Leu Arg Leu Ala Leu
        530                 535                 540

Pro Leu Arg Ser Leu Ser Ala Ser Ser Gly Trp Asn Glu Ser Cys Ser
545                 550                 555                 560

Ser Gln Ser Asp Ile Ser Leu Asp His Val Gln Arg Arg Ser Arg Leu
                565                 570                 575

Lys Glu Pro Pro Glu Leu Arg Ser Ser Glu Arg Val Ser Gly Ala Glu
                580                 585                 590

Pro Ala Pro Gly Thr Met Ser Lys His Arg Gly Lys Pro Ser Ala Ala
        595                 600                 605

Cys Arg Cys Cys Val Thr Tyr Cys Glu Gly Glu Ser His Leu Arg Ser
        610                 615                 620

Lys Ser Arg Ala Glu Met His Thr His Pro Gln Trp Glu Thr His Leu
625                 630                 635                 640

Cys Lys Pro Pro Leu Gln Glu Ser Glu Ser Gln Trp Ile Gln Asn Gly
                645                 650                 655

Thr Arg Pro Glu Pro Ala Pro Gln Ile Ser Ala Leu Ala Leu Arg His
                660                 665                 670

Phe Thr Asp Leu Ser Asn Asn Asn Asp Phe Tyr Ile Leu
        675                 680                 685
```

IL-1 RECEPTOR ACCESSORY PROTEIN

This application is a divisional of application Ser. No. 10/061,727, filed Oct. 26, 2001 (now U.S. Pat. No. 7,049,095), which claims the benefit under U.S.C. 119(e) of U.S. provisional application Ser. No. 60/244,831, filed Oct. 31, 2000. All of which is incorporated by reference herein.

BACKGROUND OF THE INVENTION

1. Field of the Invention

The invention is directed to purified and isolated IL-1 receptor family members. In particular the present invention relates of DNA encoding IL-1 Receptor Accessory Protein splice variant polypeptides, polypeptides encoded by the DNA, antibodies generated against these polypeptides, fragmented peptides derived from these polypeptides, and uses thereof.

2. Description of Related Art

Interleukin-1 (IL-1) is a member of a large group of cytokines whose primary fixation is to mediate immune and inflammatory responses. There are several members of the IL-1 ligand family, including IL-1 alpha (IL-1α), IL-1 beta (IL-1β), IL-1 eta, IL-1 receptor antagonist (IL-1ra), 1delta (IL-1δ), and IL-18 (previously known as IGIF and sometimes IL-1 gamma), IL-1 epsilon (IL-1ε), and IL-1 zeta (IL-1). IL-1 that is secreted by macrophages is actually a mixture of mostly IL-1β and some IL-1α (Abbas et al., 1994). IL-1β and IL-1α are the products of two different genes located on chromosome 2. IL-1β and IL-1α are synthesized as precursors without leader sequences and require specific cellular proteases to process to their mature forms. Although the two forms are less than 30 percent homologous to each other, they both bind to the same receptors and have similar activities.

IL-1ra is a biologically inactive form of IL-1 that is structurally homologous to IL-1 and binds to the same receptors. In contrast to IL-1β and IL-1α IL-1ra is produced with a signal sequence which allows for efficient secretion into the extracellular region where it competitively competes with IL-1 for binding IL-1 receptors. (Abbas et al., 1994).

The actions of IL-1 are mediated through interaction with the type I IL-1 receptor. IL-1 binding to the type I receptor allows the IL-1/IL-1 receptor binding complex to interact with a another protein of similar structure, called IL-1 receptor accessory proteins (IL-1 AcP), to form a ternary complex. The ternary complex initiates a signaling response that includes the association of the cytoplasmic domains of the IL-1 receptor and IL-1R AcP with MyD88, IRAK-1, IRAK-2, IRAK-M, and TRAF6.

The biological functions of IL-1 include activating vascular endothelial cells and lymphocytes, local tissue destruction, and fever (Janeway et al., 1996). At low levels, IL-1 stimulates macrophages and vascular endothelial cells to produce IL-6, upregulates molecules on the surface of vascular endothelial cells to increase leukocyte adhesion, and indirectly activates inflammatory leukocytes by stimulating mononuclear phagocytes and other cells to produce certain chemokines that activate inflammatory leukocytes. Additionally, IL-1 is involved in other inflammatory responses such as induction of prostaglandins, nitric oxide synthetase, and metalloproteinases. These IL-1 functions are crucial during low level microbial infections. However, if the microbial infection escalates, IL-1 acts systemically by inducing fever, stimulating mononuclear phagocytes to produce IL-1 and IL-6, increasing the production of serum proteins from hepatocytes, and activating the coagulation system. IL-1 has been implicated in chronic inflammatory diseases, such as rheumatoid arthritis and inflammatory bowel disease. There is increasing evidence that IL-1 plays a role in osteoporosis. All of these activities are initiated by the signaling function of the cytoplasmic portion of the type I IL-1R and the IL-1R AcP. Given the important function of IL-1 and IL-1R, there is a need in the art for additional cytokine receptors similar to the IL-1R family. Despite the growing body of knowledge, there is still a need in the art for the identity and function of proteins involved in cellular and immune responses.

SUMMARY OF THE INVENTION

Figure 1:
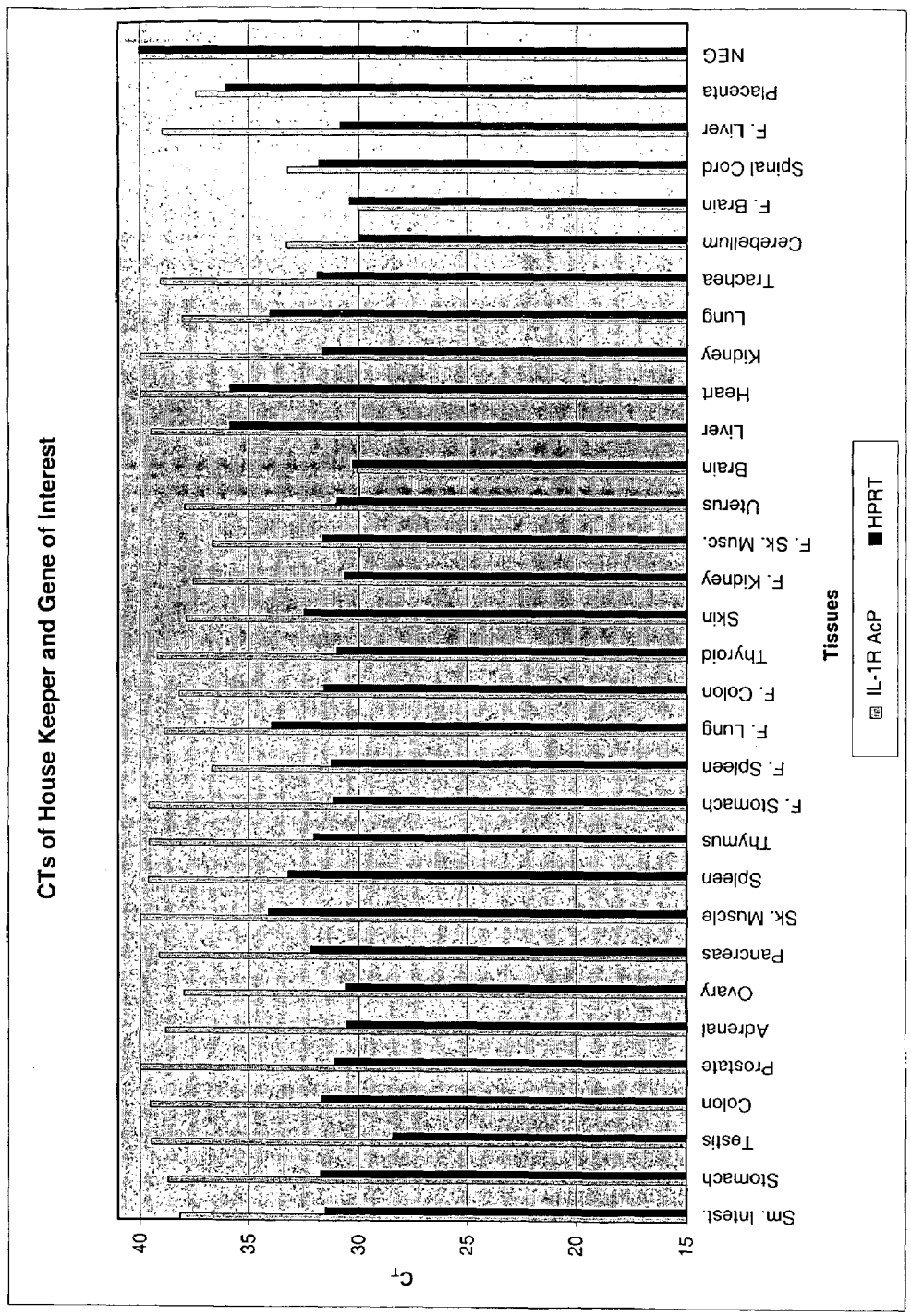
FIG. 1 shows results of a Taqman RNA expression analysis of a variety of tissue. The Figure illustrates that the IL-1R AcP of this invention is largely expressed in brain.

The present invention provides IL-1R AcP polypeptides and polynucleotides that encode the polypeptides. The invention also encompasses vectors that incorporate the polynucleotides of the invention and vectors that direct the expression of the herein described IL-1R AcP polypeptides. Further included are host cells that incorporate the vectors described herein and host cells that are stably or transiently transformed or transfected with these vectors. The present invention further provides antibodies that specifically bind IL-1R AcP polypeptides of this invention and fragments thereof, including the cytoplasmic domain.

In addition, the invention encompasses methods of using IL-1R AcP polypeptides of this invention and active fragments of IL-1R AcP to screen for antagonists and agonists of IL-1R AcP signal transduction for use as therapeutics for diseases mediated by IL-1 family members. The invention also encompasses the use of sense or antisense oligonucleotides to inhibit the expression of IL-1R AcP polypeptides. The invention further encompasses methods for the production of these polypeptides, including culturing a host cell under conditions promoting expression and recovering the polypeptide from the culture medium.

Further, methods of using these polypeptides in the design of inhibitors thereof are also an aspect of the invention.

DETAILED DESCRIPTION OF THE INVENTION

The present invention provides human and mouse IL-1R AcP polynucleotides and polypeptides encoded by the human and mouse IL-1R AcP polynucleotides, respectively. In one embodiment, the present invention provides a human IL-1R AcP polynucleotide splice variant shown in SEQ ID NO:1, the encoded polypeptide shown in SEQ ID NO:2, active polypeptide fragments of the human splice variant and polynucleotides encoding such fragments. In yet another embodiment, the present invention provides mouse IL-1R AcP polynucleotide splice variant shown in SEQ ID NO:3, the encoded polypeptide shown in SEQ ID NO:4, active polypeptide fragments of the mouse splice variant and polynucleotides encoding such fragments.

The IL-1R AcP mouse and human nucleotide sequences and their encoded amino acid sequences are shown below:

Human IL-1R AcP Polynucleotide:

(SEQ ID NO:1)

```
   1 ATGACACTTC TGTGGTGTGT AGTGAGTCTC TACTTTTATG GAATCCTGCA
  51 AAGTGATGCC TCAGAACGCT GCGATGACTG GGGACTAGAC ACCATGAGGC
 101 AAATCCAAGT GTTTGAAGAT GAGCCAGCTC GCATCAAGTG CCCACTCTTT
 151 GAACACTTCT TGAAATTCAA CTACAGCACA GCCCATTCAG CTGGCCTTAC
 201 TCTGATCTGG TATTGGACTA GGCAGGACCG GGACCTTGAG GAGCCAATTA
 251 ACTTCCGCCT CCCCGAGAAC CGCATTAGTA AGGAGAAAGA TGTGCTGTGG
 301 TTCCGGCCCA CTCTCCTCAA TGACACTGGC AACTATACCT GCATGTTAAG
 351 GAACACTACA TATTGCAGCA AAGTTGCATT TCCCTTGGAA GTTGTTCAAA
 401 AAGACAGCTG TTTCAATTCC CCCATGAAAC TCCCAGTGCA TAAACTGTAT
 451 ATAGAATATG GCATTCAGAG GATCACTTGT CCAAATGTAG ATGGATATTT
 501 TCCTTCCAGT GTCAAACCGA CTATCACTTG GTATATGGGC TGTTATAAAA
 551 TACAGAATTT TAATAATGTA ATACCCGAAG GTATGAACTT GAGTTTCCTC
 601 ATTGCCTTAA TTTCAAATAA TGGAAATTAC ACATGTGTTG TTACATATCC
 651 AGAAAATGGA CGTACGTTTC ATCTCACCAG GACTCTGACT GTAAAGGTAG
 701 TAGGCTCTCC AAAAAATGCA GTGCCCCCTG TGATCCATTC ACCTAATGAT
 751 CATGTGGTCT ATGAGAAAGA ACCAGGAGAG GAGCTACTCA TTCCCTGTAC
 801 GGTCTATTTT AGTTTTCTGA TGGATTCTCG CAATGAGGTT TGGTGGACCA
 851 TTGATGGAAA AAAACCTGAT GACATCACTA TTGATGTCAC CATTAACGAA
 901 AGTATAAGTC ATAGTAGAAC AGAAGATGAA ACAAGAACTC AGATTTTGAG
 951 CATCAAGAAA GTTACCTCTG AGGATCTCAA GCGCAGCTAT GTCTGTCATG
1001 CTAGAAGTGC CAAAGGCGAA GTTGCCAAAG CAGCCAAGGT GAAGCAGAAA
1051 GTGCCAGCTC CAAGATACAC AGTGGAACTG GCTTGTGGTT TTGGAGCCAC
1101 AGTCCTGCTA GTGGTGATTC TCATTGTTGT TTACCATGTT TACTGGCTAG
1151 AGATGGTCCT ATTTTACCGG GCTCATTTTG GAACAGATGA AACCATTTTA
1201 GATGGAAAAG AGTATGATAT TTATGTATCC TATGCAAGGA ATGCGGAAGA
1251 AGAAGAATTT GTATTACTGA CCCTCCGTGG AGTTTTGGAG AATGAATTTG
1301 GATACAAGCT GTGCATCTTT GACCGAGACA GTCTGCCTGG GGGAAATACA
1351 GTGGAAGCAG TTTTTGATTT CATTCAGAGA AGCAGAAGGA TGATTGTTGT
1401 TCTGAGCCCT GACTATGTGA CAGAAAAGAG CATCAGCATG CTGGAGTTTA
1451 AACTGGGTGT CATGTGCCAG AACTCCATTG CCACCAAGCT CATTGTGGTT
1501 GAGTACCGTC CCCTTGAGCA CCCGCACCCA GGCATTCTTC AGCTCAAAGA
1551 GTCTGTGTCT TTTGTGAGCT GGAAGGGAGA AAAGTCCAAA CATTCTGGCT
1601 CTAAATTCTG GAAAGCTTTG CGGTTGGCTC TTCCCCTGAG AAGTCTGAGT
1651 GCCAGTTCTG GCTGGAATGA GAGCTGCTCT TCCCAGTCTG ACATCAGTCT
1701 GGATCACGTT CAAAGGAGGA GAAGTCGTTT GAAAGAGCCC CCAGAACTTC
1751 AGAGCTCAGA GAGGGCTGCA GGTAGCCCTC CAGCCCCAGG CACAATGTCC
1801 AAGCACCGAG GGAAGTCCTC CGCCACCTGC CGCTGTTGTG TCACCTACTG
```

-continued

```
1851 TGAAGGAGAG AATCACCTTA GGAACAAGAG CCGGGCAGAG ATTCATAACC

1901 AGCCCCAGTG GGAGACACAC CTCTGTAAGC CTGTTCCCCA AGAGTCAGAA

1951 ACTCAATGGA TACAAAATGG CACCAGATTG GAACCCCCTG CTCCCCAGAT

2001 CTCAGCCCTT GCTCTTCATC ATTTCACGGA CTTATCCAAT AACAACGACT

2051 TTTATATCCT ATAA
```

Human IL-1R AcP Splice Variant Encoded Polypeptide:

```
                                                       (SEQ ID NO:2)
    MTLLWCVVSL YFYGILQSDA SERCDDWGLD TMRQIQVFED EPARIKCPLF

51 EHFLKFNYST AHSAGLTLIW YWTRQDRDLE EPINFRLPEN RISKEKDVLW

101 FRPTLLNDTG NYTCMLRNTT YCSKVAFPLE VVQKDSCFNS PMKLPVHKLY

151 IEYGIQRITC PNVDGYFPSS VKPTITWYMG CYKIQNFNNV IPEGMNLSFL

201 IALISNNGNY TCVVTYPENG RTFHLTRTLT VKVVGSPKNA VPPVIHSPND

251 HVVYEKEPGE ELLIPCTVYF SFLMDSRNEV WWTIDGKKPD DITIDVTINE

301 SISHSRTEDE TRTQILSIKK VTSEDLKRSY VCHARSAKGE VAKAAKVKQK

351 VPAPRYTVEL ACGFGATVLL VVILIVVYHV YWLEMVLFYR AHFGTDETIL

401 DGKEYDIYVS YARNAEEEEF VLLTLRGVLE NEFGYKLCIF DRDSLPGGNT

451 VEAVFDFIQR SRRMIVVLSP DYVTEKSISM LEFKLGVMCQ NSIATKLIVV

501 EYRPLEHPHP GILQLKESVS FVSWKGEKSK HSGSKFWKAL RLALPLRSLS

551 ASSGWNESCS SQSDISLDHV QRRRSRLKEP PELQSSERAA GSPPAPGTMS

601 KHRGKSSATC RCCVTYCEGE NHLRNKSRAE IHNQPQWETH LCKPVPQESE

651 TQWIQNGTRL EPPAPQISAL ALHHFTDLSN NNDFYIL
```

Mouse IL-1R AcP Polynucleotide

```
                                                       (SEQ ID NO:3)
  1 ATGGGACTTC TGTGGTATTT GATGAGTCTG TCCTTCTATG GGATCCTGCA

51 GAGTCATGCT TCGGAGCGCT GTGATGACTG GGGACTAGAT ACCATGCGAC

101 AAATCCAAGT GTTTGAAGAT GAGCCGGCTC GAATCAAGTG CCCCCTCTTT

151 GAACACTTCC TGAAGTACAA CTACAGCACT GCCCATTCCT CTGGCCTTAC

201 CCTGATCTGG TACTGGACCA GGCAAGACCG GGACCTGGAG GAGCCCATTA

251 ACTTCCGCCT CCCAGAGAAT CGCATCAGTA AGGAGAAAGA TGTGCTCTGG

301 TTCCGGCCCA CCCTCCTCAA TGACACGGGC AATTACACCT GCATGTTGAG

351 GAACACAACT TACTGCAGCA AAGTTGCATT TCCCCTGGAA GTTGTTCAGA

401 AGGACAGCTG TTTCAATTCT GCCATGAGAT TCCCAGTGCA CAAGATGTAT

451 ATTGAACATG GCATTCATAA GATCACATGT CCAAATGTAG ACGGATACTT

501 TCCTTCCAGT GTCAAACCAT CGGTCACTTG GTATAAGGGT TGTACTGAAA

551 TAGTGGACTT TCATAATGTA CTACCCGAGG GCATGAACTT GAGCTTTTTC

601 ATCCCCTTGG TTTCAAATAA CGGAAATTAC ACATGTGTGG TTACATATCC

651 TGAAAACGGA CGTCTCTTTC ACCTCACCAG GACTGTGACT GTAAAGGTGG

701 TGGGCTCACC AAAGGATGCA TTGCCACCCC AGATCTATTC TCCAAATGAC
```

-continued

```
 751 CGTGTTGTCT ATGAGAAAGA ACCAGGAGAG GAACTGGTTA TTCCCTGCAA
 801 AGTCTATTTC AGTTTCATTA TGGACTCCCA CAATGAGGTC TGGTGGACCA
 851 TTGATGGAAA GAAGCCTGAT GACGTCACAG TCGACATCAC TATTAATGAA
 901 AGTGTAAGTT ATTCTTCAAC GGAAGATGAA ACAAGGACTC AGATTTTGAG
 951 CATCAAGAAA GTCACCCCGG AGGATCTCAG GCGCAACTAT GTCTGTCATG
1001 CTCGAAATAC CAAAGGGGAA GCTGAGCAGG CTGCCAAGGT GAAACAGAAA
1051 GTCATACCAC CAAGGTACAC AGTAGAACTC GCCTGTGGTT TTGGAGCCAC
1101 GGTCTTTCTG GTAGTGGTTC TCATTGTGGT TTACCATGTT TACTGGCTGG
1151 AGATGGTCCT CTTTTACCGA GCTCACTTTG GAACAGATGA AACAATTCTT
1201 GATGGAAAGG AGTATGATAT TTATGTTTCC TATGCAAGAA ATGTGGAAGA
1251 AGAGGAATTT GTGCTGCTGA CGCTGCGTGG AGTTTTGGAG AATGAGTTTG
1301 GATACAAGCT GTGCATCTTC GACAGAGACA GCCTGCCTGG GGGAAATACC
1351 GTGGAAGCAG TTTTTGATTT CATTCAGAGG AGCCGAAGGA TGATTGTTGT
1401 CCTGAGCCCT GACTATGTGA CAGAAAAGAG CATCAGCATG CTGGAGTTTA
1451 AGCTGGGTGT CATGTGCCAG AACTCCATTG CCACTAAGCT CATTGTGGTG
1501 GAGTACCGTC CGCTTGAGCA ACCCCATCCA GGCATCATGC AGCTGAAGGA
1551 GTCTGTGTCT TTTGTAAGCT GGAAGGGAGA AAAGTCCAAA CATTCTGGCT
1601 CCAAGTTCTG GAAGGCCTTG CGTTTGGCTC TTCCCCTGAG AAGTCTGAGC
1651 GCCAGCTCCG GCTGGAATGA GAGCTGTTCT TCTCAGTCTG ACATCAGTCT
1701 GGATCATGTT CAGAGGAGAA GTCGTTTGAA AGAGCCCCCA GAACTCCGAA
1751 GCTCAGAGAG GGTGTCTGGA GCAGAGCCAG CCCCGGGCAC GATGTCCAAG
1801 CACCGAGGGA AACCCTCAGC AGCCTGTCGC TGCTGTGTCA CCTACTGTGA
1851 AGGAGAAAGT CACCTCAGGA GCAAGAGCCG GGCAGAGATG CACACGCATC
1901 CCCAGTGGGA AACACACCTC TGTAAGCCTC CTCTCCAAGA GTCTGAAAGT
1951 CAGTGGATAC AAAATGGCAC CCGACCCGAA CCCGCTCCCC AGATCTCAGC
2001 TCTTGCACTC CGCCACTTTA CAGATTTATC CAATAACAAT GACTTTTATA
2051 TCCTATAA
```

Mouse IL-1R AcP Polypeptide:

```
                                                   (SEQ ID NO:4)
  1 MGLLWYLMSL SFYGILQSHA SERCDDWGLD TMRQIQVFED EPARIKCPLF
 51 EHFLKYNYST AHSSGLTLIW YWTRQDRDLE EPINFRLPEN RISKEKDVLW
101 FRPTLLNDTG NYTCMLENTT YCSKVAFPLE VVQKDSCFNS ANRFPVHKMY
151 IEHGIHKITC PNVDGYFPSS VKPSVTWYKG CTEIVDFHNV LPEGNNLSFF
201 IPLVSNNGNY TCVVTYPENG RLFHLTRTVT VKVVGSPKDA LPPQIYSPND
251 RVVYEKEPGE ELVIPCKVYF SFIMDSHNEV WWTIDGKKPD DVTVDITINE
301 SVSYSSTEDE TRTQILSIKK VTPEDLRENY VCHARNTKGE AEQAAKVKQK
351 VIPPRYTVEL ACGFGATVFL VVVLIVVYHV YWLEMVLFYR AHFGTDETIL
401 DGKEYDIYVS YARINEEEEF VLLTLRGVLE NEFGYKLCIF DRDSLPGGNT
```

```
-continued
451 VEAVFDFIQR SRRMIVVLSP DYVTEKSISM LEFKLGVMCQ NSIATKLIVV

501 EYRPLEQPHP GIMQLKESVS FVSWKGEKSK HSGSKFWKAL RLALPLRSLS

551 ASSGWNESCS SQSDISLDHV QRRSRLKEPP ELRSSERVSG AEPAPGTMSK

601 HRGKPSAACR CCVTYCEGES HLRSKSRAEM HTHPQWETHL CKPPLQESES

651 QWIQNGTRPE PAPQISALAL RHFTDLSNNN DFYIL*
```

The native human IL-1R AcP of this invention includes a polymorphism that is present at about a 50/50 ratio. The polymorphism exists as an A at position 1792 of SEQ ID NO:1, or a C at position 1792 of SEQ ID NO:1. This results in a Thr at position 598 of SEQ ID NO:2, or a Pro at position 598 or SEQ ID NO:2.

The human IL-1R AcP polypeptide of the present invention is homologous to IL-1 receptor type I and its known homologs and shares an overall 83% amino acid identity with the human IL-1R AcP described in WO96/23067, of which it is a splice variant. The IL-1R AcP polypeptides and polynucleotides of this invention are an alternatively spliced variant of IL-1R AcP in which part of the C-terminus of the cytoplasmic domain is replaced by an alternative peptide sequence. At least part of this alternative peptide sequence is amino acids 449-687 of SEQ ID NO:2 and amino acids 449-685 of SEQ ID NO:4, both of which are encompassed by this invention.

The IL-1R AcP polypeptides described herein are type I transmembrane proteins with an extracellular region, a transmembrane region and a cytoplasmic region. In one embodiment of the present invention, the human polypeptide of SEQ ID NO:2 includes an extracellular region having amino acids 1-362, a transmembrane region that includes amino acids 363-383 and a cytoplasmic regions that includes amino acids 384-687. The signal peptide includes amino acids 1-17 of the extracellular domain, which may alternatively include amino acids 18-362. These regions are encoded by nucleotides as follows 1-1086 encoding extracellular domain, (1-51 being the signal peptide) 1087-1149 encoding the transmembrane region, and 1150-2064, encoding the cytoplasmic domain, all of SEQ ID NO:1. The invention includes polynucleotides that encode the polypeptide of SEQ ID NO:2 and polynucleotides the encode the transmembrane region and the cytoplasmic region of the human IL-1R AcP shown in SEQ ID NO:2. Thus, for example, the present invention includes the coding region of SEQ ID NO:1 and polynucleotides represented by nucleotides residues 1150-2061 and exon 1346-2061 of SEQ ID NO:1

In another embodiment, the human polypeptide of SEQ ID NO:2 includes an extracellular region having amino acids 1-359, a transmembrane region that includes amino acids 360-378 and a cytoplasmic regions that includes amino acids 379-687. In this embodiment the signal peptide includes amino acids 1-17 of the extracellular domain, which may alternatively include amino acids 18-359. These regions are encoded by nucleotides as follows 1-1077 encoding extracellular domain, (1-51 being the signal peptide) 1078-1134 encoding the transmembrane region, and 1135-2061, encoding the cytoplasmic domain, all of SEQ ID NO:1 and exon 1346-2064 of SEQ ID NO:1

Similarly, in one embodiment, the mouse IL-1R AcP splice variant of SEQ ID NO:4 has an extracellular region that includes amino acids 1-367 (1-17 being the signal peptide, so that amino acid 18-367 is also the extracellular region), a transmembrane region that includes amino acids 368-388 and a cytoplasmic region that includes amino acids 389-685, all of SEQ ID NO:4. These regions are encoded by the following nucleotide: nucleotides 1-1101, which encode the extracellular domain (1-51 encoding the signal peptide); 1102-1164 which encode the transmembrane region; and nucleotides 1165-2058 which encode the cytoplasmic domain, all of SEQ ID NO:3. Nucleotide residues that encode the new exon include nucleotides 1346-2058. It is understood that this invention includes polynucleotides that are degenerate to the above noted encoding polynucleotides of SEQ ID NO:1 and SEQ ID NO:3

Similarly, in another embodiment, the mouse IL-1R AcP splice variant of SEQ ID NO:4 has an extracellular region that includes amino acids 1-359 (1-17 of this being the signal peptide) so that amino acid 18-359 is an alternate extracellular domain, a transmembrane region that includes amino acids 360-378 and a cytoplasmic region that includes amino acids 379-685, all of SEQ ID NO:4. These regions are encoded by the following: nucleotides 1-1077, which encode the extracellular domain (1-51 encoding the signal peptide); 1078-1134 which encode the transmembrane region; and nucleotides 1135-2055 which encode the cytoplasmic domain, all of SEQ ID NO:3. Nucleotide residues that encode the new exon include nucleotides 1346-2055. It is understood that this invention includes polynucleotides that are degenerate to the above noted encoding polynucleotides of SEQ ID NO:1 and SEQ ID NO:3

The discovery of polynucleotides that encode the human and mouse IL-1R AcP polypeptides described herein enables the construction of expression vectors that incorporate polynucleotides of this invention. This discovery further enables the construction of host cells transfected or transformed with the expression vectors, and, enables the construction of host cells that include the encoding polynucleotides. The vectors and host cells of the present invention are useful for expressing IL-1R AcP polypeptides and fragments thereof that are described herein.

The actions of IL-1 family members are mediated through a signaling response that includes the association of the cytoplasmic domains of the IL-1 receptor and/or members of the IL-1 receptor family which include but are not limited to SIGIRR (see WO 99/32626) TIGIRR (see WO99/32629), Xrec2 (APL) (See WO 00/36108) or IL-1R AcP with a number of intracellular proteins which may include but are not limited to MyD88, IRAK-1, IRAK-2, IRAK-M and TRAF6. IL-1 family members include IL-1α, IL-1β, IL-1 receptor antagonist, IL-18, and IL-1F5-IL-1F10, all as described and referenced in TRENDS in Immunology, Vol. 22 No. 10, October 2001. Thus, the ability to antagonize or agonize the association of the IL-1R AcP of the present invention with one or more intracellular signaling transduction factor proteins provides a pathway to modulate the actions of IL-1 family members. An antagonist of a proinflammatory IL-1 family member can be used for the inhibition and/or prevention of disease and medical conditions associated with that IL-1 family member expression. Similarly, an agonist of an IL-1 family member that has a negative or regulatory role in signaling can be used for the inhibition and/or prevention of inflammatory disease. As described below, the IL-1R AcP polypeptides of the present invention are expressed in brain and central nervous system (CNS) tissue and thus play a role in modulating inflammatory and immune responses associated with brain and CNS tissue.

In a particular embodiment, the present invention relates to certain isolated polynucleotides that are free from contaminating endogenous material. A "polynucleotide" refers to a molecule in the form of a separate fragment or as a component of a larger polynucleic acid construct. Such polynucleotides are preferably represented by and/or constructed in the form of open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

Polynucleotides of the invention include DNA in both single-stranded and double-stranded form, as well as the RNA complement thereof. DNA includes, for example, cDNA, genomic DNA, chemically synthesized DNA, DNA amplified by PCR, and combinations thereof. Genomic DNA may be isolated by conventional techniques, e.g., using the polynucleotide of SEQ ID NO:1 wherein the nucleotide at position 1792 is A or C, or SEQ ID NO:3, or a suitable fragment thereof, as a probe in PCR reactions.

The polynucleotides of the invention include full-length genes and fragments that are useful as described herein. The full-length gene may include the N-terminal signal peptide or it may exclude the signal peptide. Alternatively, full-length polynucleotides of this invention encompass the polynucleotide excluding the native signal peptide and incorporating a different signal peptide. Suitable fragments of the polynucleotides include those that encode the cytoplasmic domain and portions of the cytoplasmic domain that are capable of interacting with, modulating or binding signal transduction factors, including but not limited to, MyD88, IRAK-1, IRAK-2, IRAK-M and TRAF6. Preferred polynucleotides of the present invention are those that encode the polypeptides of SEQ ID NO:2, wherein the amino acid residue at position 598 is a Thr or Pro, and SEQ ID NO:4, e.g. the polynucleotides of SEQ ID NO:1 and SEQ ID NO:3, respectively, wherein the nucleotide at position 1792 of SEQ ID NO:1 is A or C. Useful polynucleotide fragments of the present invention include those that encode a cytoplasmic domain of SEQ ID NO:2 and SEQ ID NO:4, i.e. amino acid residues 384-687 of SEQ ID NO:2, wherein the amino acid residue at position 598 is Thy or Pro, and amino acid residues 389-685 of SEQ ID NO:4. Embodiments of nucleotides that encode the cytoplasmic domain of the described polypeptides include nucleotide residues 1150-2064 of SEQ ID NO:1, wherein the nucleotide at position 1792 is A or C, and 1165-2058 of SEQ ID NO:3.

Additional useful polynucleotide fragments of the present invention include those that encode amino acid residues 379-687 of SEQ ID NO:2, wherein the amino acid residue at position 598 is Thy or Pro, and amino acid residues 379-685 of SEQ ID NO:4. Another fragment includes amino acids 649-687 of SEQ ID NO:2 and amino acids 649-685 of SEQ ID NO:4. Embodiments of nucleotides that encode just described polypeptides include nucleotide residues 1135-2061 of SEQ ID NO:1 and 1346-2061 of SEQ ID NO:1, wherein the nucleotide at position 1792 is A or C, and 1165-2058 and nucleotide 1346-2055, both of SEQ ID NO:3.

Polynucleotides of this invention include those that are degenerate to SEQ ID NO:1, SEQ ID NO:3 and fragments that encode biologically active polypeptide, including those described above. Degenerate polynucleotides arise because of the known degeneracy of the genetic code, wherein more than one codon can encode the same amino acid, a polynucleotide can vary from that shown in the coding sequences of SEQ ID NO:1 and SEQ ID NO:3 and still encode a polypeptide having the amino acid sequence of SEQ ID NO:2 and SEQ ID NO:4, respectively. Such variant polynucleotides can result from silent mutations (e.g., occurring during PCR amplification), or can be the product of deliberate mutagenesis of a native sequence.

The present invention thus provides isolated DNAs that include (a) SEQ ID NO:1 wherein the nucleotide at position 1792 is A or C; (b) SEQ ID NO:3; (c) DNA encoding the polypeptide of SEQ ID NO:2, wherein the amino acid residue at 598 is Pro or Thr.; (d) DNA encoding the polypeptide of SEQ ID NO:4; (e) DNA encoding the polypeptide having amino acid residues 449-687 of SEQ ID NO:2, wherein the residue at 598 is Thr or Pro; (f) DNA encoding a polypeptide having amino acid residues 449-685 of SEQ ID NO:4, (g) DNA encoding a polypeptide having amino acid residues 384-687 of SEQ ID NO:2, wherein the amino acid residue at 598 is Pro or Thr; (h) DNA encoding amino acid residues 379-687 of SEQ ID NO:2, wherein the amino acid residues at 598 is Pro or Thr, (i) DNA encoding a polypeptide having amino acid residues 389-685 of SEQ ID NO:4; (j) DNA encoding a polypeptide having amino acid residues 379-685 of SEQ ID NO:4 (k) DNA encoding a polypeptide that is a fragment of the polypeptide having amino acid residues 384-687 of SEQ ID NO:2, wherein the amino acid residue at 598 is Thr or Pro; the fragment capable of interacting with an intracellular signal transduction factor; (l) DNA encoding a polypeptide that is a fragment of the polypeptide having amino acids residues 379-687 of SEQ ID NO:2, wherein the amino acid residue at 598 is Thr or Pro, the fragment capable of interacting with an intracellular signal transduction factor; (m) DNA encoding a polypeptide that is a fragment of the polypeptide having amino acid residues 389-685 of SEQ ID NO:4; the fragment capable of interacting with an intracellular signal transduction factor; (n) DNA encoding a polypeptide that is a fragment of the polypeptide having amino acid residues 379-685 of SEQ ID NO:4, the fragment capable of interacting with an intracellular signal transduction factor; (o) DNA that is the complement of a DNA capable of hybridization to a DNA of (a) through (n) under conditions of moderate stringency; and, (p) DNA which is degenerate as a result of the genetic code to a DNA defined in (a)-(o).

As used herein, conditions of moderate stringency can be readily determined by those having ordinary skill in the art based on, for example, the length of the DNA. The basic conditions are set forth by Sambrook et al. *Molecular Cloning: A Laboratory Manual*, 2 ed. Vol. 1, pp. 1.10 1-104, Cold Spring Harbor Laboratory Press, (1989), and inolude use of a prewashing solution for the nitrocellulose filters 5×SSC, 0.5% SDS, 1.0 mM EDTA (pH8.0), hybridization conditions of about 50% formamide, 6×SSC at about 42° C. (or other similar hybridization solution, such as Stark's solution, in about 50% formamide at about 42° C.), and washing conditions of about 60° C., 0.5×SSC, 0.1% SDS. Conditions of high stringency can also be readily determined by the skilled artisan based on, for example, the length of the DNA. Generally, such conditions are defined as hybridization conditions as above, and with washing at approximately 68° C., 0.2×SSC, 0.1% SDS. The skilled artisan will recognize that the temperature and wash solution salt concentration can be adjusted as necessary according to factors such as the length of the probe.

The present invention further includes DNA encoding polypeptide fragments and polypeptides comprising inactivated N-glycosylation site(s), inactivated protease processing site(s), or conservative amino acid substitution(s), as described below.

In another embodiment, the polynucleotides of this invention include variant polynucleotides that are at least 85% identical to the polynucleotides that encode the cytoplasinic domain of SEQ ID NO:2 and SEQ ID NO:4. Similarly, the present invention includes polynucleotides that are at least 80% identical to polynucleotides that encode polypeptide fragments of the cytoplasmic domain of SEQ ID NO:2 and SEQ ID NO:4 when the polypeptide fragments are capable of interacting with a signal transduction factor, including but not limited to MyD88, IRAK-1, IRAK-2, IRAK-M, and TRAF6

The percent identity may be determined by visual inspection and mathematical calculation. Alternatively, the percent identity of two nucleic acid sequences can be determined by comparing sequence information using the GAP computer program, version 6.0 described by Devereux et al. (*Nucl. Acids Res.* 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353-358, 1979; (2) a penalty of 3.0 for each gap and an additional 0.10 penalty for each symbol in each gap; and (3) no penalty for end gaps. Other programs used by one skilled in the art of sequence comparison may also be used.

The polynucleotides of this invention are useful in processes for preparing polypeptides that are disclosed herein. For example, a DNA encoding a polypeptide of the present invention, or polypeptide fragment of this invention may be subcloned into an expression vector for production of the polypeptide or polypeptide fragment. The DNA advantageously is fused to a polynucleotide encoding a suitable leader or signal peptide. Alternatively, a polynucleotide described herein or suitable fragment may be chemically synthesized using known techniques. DNA fragments may be prepared by restriction endonuclease digestion of a full length cloned DNA sequence, and isolated by electrophoresis on agarose gels. If necessary, oligonucleotides that reconstruct the 5' or 3' terminus to a desired point may be ligated to a DNA fragment generated by restriction enzyme digestion. Such oligonucleotides may additionally contain a restriction endonuclease cleavage site upstream of the desired coding sequence, and position an initiation codon (ATG) at the N-terminus of the coding sequence.

The well-known polymerase chain reaction (PCR) procedure also may be employed to isolate and amplify a DNA encoding a desired polypeptide fragment. Oligonucleotides that define the desired termini of the DNA fragment are employed as 5' and 3' primers. The oligonucleotides may contain recognition sites for restriction endonucleases, to facilitate insertion of the amplified DNA fragment into an expression vector. PCR techniques are described in Saiki et al., *Science* 239:487 (1988); *Recombinant DNA Methodology*, Wu et al., eds., Academic Press, Inc., San Diego (1989), pp. 189-196; and *PCR Protocols: A Guide to Methods and Applications*, Innis et al., eds., Academic Press, Inc. (1990).

IL-1R AcP polypeptides of the present invention include those that are naturally occurring and variant polypeptides that are produced through various techniques such as procedures involving recombinant DNA technology. For example, DNAs encoding polypeptides described herein can be derived from SEQ ID NO:1 and/or SEQ ID NO:3 as described above, by in vitro mutagenesis, which includes site-directed mutagenesis, random mutagenesis, and in vitro nucleic acid synthesis. Such forms include, but are not limited to, derivatives, variants, and oligomers, as well as polynucleotides that encode fusion proteins or fragments thereof.

The polypeptides of the invention include full-length proteins encoded by the polynucleotides set forth above. A preferred human polypeptide includes the amino acid residues of SEQ ID NO:2, wherein the amino acid residue at 598 is Pro or Thr; and, a preferred mouse polypeptide includes the amino acid residues of SEQ ID NO:4. Further, the invention encompasses fragments and domains of the polypeptides of SEQ ID NO:2 and SEQ ID NO:4 including the cytoplasmic domains of SEQ ID NO:2 and SEQ ID NO:4. In particular such fragments include amino acids 384-687 of SEQ ID NO:2, amino acids 379-687 of SEQ ID NO:2, wherein the amino acids residue at 598 is Pro or Thr; amino acids 389-685 of SEQ ID NO:4, amino acids 379-685 of SEQ ID NO:4; polypeptide fragments of amino acids 384-687 of SEQ ID NO:2, polypeptide fragments of amino acid residues 379-687 of SEQ ID NO:2; polypeptide fragments of amino acids 389-685 of SEQ ID NO:4, polypeptide fragments of amino acids residues 379-685 of SEQ ID NO:4, where the above mentioned fragments interact with a intracellular signal transduction factor. Other useful fragments include amino acids 449-687 of SEQ ID NO:2 and amino acids 449-685 of SEQ ID NO:4.

The polypeptides of the invention may be membrane bound or they may be secreted and thus soluble. Soluble polypeptides are capable of being secreted from the cells in which they are expressed. In general, soluble polypeptides may be identified (and distinguished from non-soluble membrane-bound counterparts) by separating intact cells which express the desired polypeptide from the culture medium, e.g., by centrifugation, and assaying the medium (supernatant) for the presence of the desired polypeptide. The presence of polypeptide in the medium indicates that the polypeptide was secreted from the cells and thus is a soluble form of the protein.

Also provided herein are polypeptide fragments comprising at least 20, or at least 30, contiguous amino acids of the polypeptide 449-687 of SEQ ID NO:2 and the polypeptide of 449-685 of SEQ ID NO:4. The position at 598 of SEQ ID NO:2 may be Pro or Thr. As discussed below and mentioned above, fragments derived from the cytoplasmic domain find use in studies of signal transduction, and in regulating cellular processes associated with transduction of biological signals. Polypeptide fragments also may be employed as immunogens, in generating antibodies.

A polypeptide variant as referred to herein means a polypeptide substantially homologous to native IL-1R AcP polypeptide described herein, but which has an amino acid sequence different from that of the disclosed native IL-1R AcP polypeptides because of one or more deletions, insertions, or substitutions. A variant polypeptide has an amino acid sequence that preferably is at least 85% identical to a native polypeptide amino acid sequence, most preferably at least 90% identical. The percent identity may be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353-358, 1979; (2) a penalty of 3.0 for each gap and an additional 0.10 penalty for each symbol in each gap; and (3) no penalty for end gaps.

Variants also include embodiments in which a polypeptide or fragment comprises an amino acid sequence that is at least 85% identical, at least 90% identical, at least 95% identical, and at least 98% identical to preferred polypeptide or fragment thereof. Such variant further retains an activity that is characteristic of the IL-1R AcP of this invention. One example is a variant that interacts with an IL-1 receptor family member or IL-1 in a signaling complex. Another example is a polypeptide or this invention, including fragments and variants having the capacity to interact with or modulate intracellular signal transduction factors, including IRAK-1, IRAK-2, IRAK-M, and TRAFs. Yet, another example is a variant that retains similar binding affinity or similar as an IL-1R AcP polypeptide of this invention, including fragments and variants. Binding affinity can be measured by conventional procedures, e.g., as described in U.S. Pat. No. 5,512,457. Similarly, variant cytoplasmic domain polypeptides include polypeptides that retain at least an 80% amino acid identity with the cytoplasmic domain of SEQ ID NO:2 or SEQ ID NO:4 and which interact with signal transduction factors.

Percent identity may be determined as above. Alternatively, the percent identity of two protein sequences can be determined by comparing sequence information using the GAP computer program, based on the algorithm of Needleman and Wunsch (J. Mol. Bio. 48:443, 1970) and available from the University of Wisconsin Genetics Computer Group (UWGCG). The preferred default parameters for the GAP program include: (1) a scoring matrix, blosum62, as described by Henikoff and Henikoff (*Proc. Natl. Acad. Sci.* USA 89:10915, 1992); (2) a gap weight of 12; (3) a gap length weight of 4; and (4) no penalty for end gaps. Other programs used by one skilled in the art of sequence comparison may also be used.

The variants of the invention include, for example, those that result from alternate mRNA splicing events or from proteolytic cleavage. Alternate splicing of mRNA may, for example, yield a truncated but biologically active protein, such as a naturally occurring soluble form of the protein. Variations attributable to proteolysis include, for example, differences in the N- or C-termini upon expression in different types of host cells, due to proteolytic removal of one or more terminal amino acids from the protein (generally from 1-5 terminal amino acids). Proteins in which differences in amino acid sequence are attributable to genetic polymorphism (allelic variation among individuals producing the protein) are also contemplated herein.

As stated above, the invention provides isolated and purified, or homogeneous, IL-1R AcP polypeptides, both recombinant and non-recombinant. Variants and derivatives of native polypeptides that retain the desired biological activity can be obtained by mutations of nucleotide sequences coding for native IL-1R AcP polypeptides of this invention. Alterations of the native amino acid sequence can be accomplished by any of a number of conventional methods. Mutations can be introduced at particular loci by synthesizing oligonucleotides containing a mutant sequence flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene, wherein predetermined codons can be altered by substitution, deletion, or insertion. Exemplary methods of making the alterations set forth above are disclosed by Walder et al. (*Gene* 42:133, 1986); Bauer et al. (*Gene* 37:73, 1985); Craik (*BioTechniques*, January 1985, 12-19); Smith et al. (*Genetic Engineering: Principles and Methods*, Plenum Press, 1981); Kunkel (*Proc. Natl. Acad. Sci.*USA 82:488, 1985); Kunkel et al. (*Methods in Enzymol.* 154:367, 1987); and U.S. Pat. Nos. 4,518,584 and 4,737,462, all of which are incorporated by reference.

Polypeptides can be modified to create polypeptide derivatives encompassed by this invention by forming covalent or aggregative conjugates with other chemical moieties, such as glycosyl groups, polyethylene glycol (PEG) groups, lipids, phosphate, acetyl groups and the like. Covalent derivatives of the disclosed IL-1R AcP polypeptides can be prepared by linking the chemical moieties to functional groups on IL-1R AcP amino acid side chains or at the N-terminus or C-terminus of a polypeptide or the extracellular domain thereof. Other derivatives of the native polypeptides described herein within the scope of this invention include covalent or aggregative conjugates of native polypeptides or their fragments with other proteins or polypeptides, such as by synthesis in recombinant culture as N-terminal or C-terminal fusions. For example, the conjugate can comprise a signal or leader polypeptide sequence (e.g. the α-factor leader of *Saccharomyces*) at the N-terminus of an IL-1R AcP polypeptide. The signal or leader peptide co-translationally or post-translationally directs transfer of the conjugate from its site of synthesis to a site inside or outside of the cell membrane or cell wall.

Conjugates comprising diagnostic (detectable) or therapeutic agents attached thereto are contemplated herein, as discussed in more detail below.

Other derivatives include covalent or aggregative conjugates of the polypeptides with other proteins or polypeptides, such as by synthesis in recombinant culture as N-terminal or C-terminal fusions. Examples of fusion proteins are discussed below in connection with oligomers. Further, fusion proteins can comprise peptides added to facilitate purification and identification. Such peptides include, for example, poly-His or the antigenic identification peptides described in U.S. Pat. No. 5,011,912 and in Hopp et al., *Bio/Technology* 6:1204, 1988. One such peptide is the FLAG® peptide, Asp-Tyr-Lys-Asp-Asp-Asp-Asp-Lys, which is highly antigenic and provides an epitope reversibly bound by a specific monoclonal antibody, enabling rapid assay and facile purification of expressed recombinant protein. A murine hybridoma designated 4E11 produces a monoclonal antibody that binds the FLAG® peptide in the presence of certain divalent metal cations, as described in U.S. Pat. No. 5,011,912, hereby incorporated by reference. The 4E11 hybridoma cell line has been deposited with the American Type Culture Collection under accession no. HB 9259. Monoclonal antibodies that bind the FLAG® peptide are available from Eastman Kodak Co., Scientific Imaging Systems Division, New Haven, Conn.

Variants include polypeptides that are substantially homologous to the native form, but which have an amino acid sequence different from that of the native form because of one or more deletions, insertions or substitutions. Particular embodiments include, but are not limited to, polypeptides that comprise from one to ten deletions, insertions or substitutions of amino acid residues, when compared to a native sequence. A given amino acid may be replaced, for example, by a residue having similar physiochemical characteristics. Examples of such conservative substitutions include substitution of one aliphatic residue for another, such as Ile, Val, Leu, or Ala for one another; substitutions of one polar residue for another, such as between Lys and Arg, Glu and Asp, or Gln and Asn; or substitutions of one aromatic residue for another, such as Phe, Trp, or Tyr for one another. Other conservative substitutions, e.g., involving substitutions of entire regions having similar hydrophobicity characteristics, are well known.

Similarly, the DNAs of the invention include variants that differ from a native DNA sequence because of one or more deletions, insertions or substitutions, but that encode a biologically active polypeptide.

The invention further includes polypeptides of the invention with or without associated native-pattern glycosylation. Polypeptides expressed in yeast or mammalian expression systems (e.g., COS-1 or COS-7 cells) can be similar to or significantly different from a native polypeptide in molecular weight and glycosylation pattern, depending upon the choice of expression system. Expression of polypeptides of the invention in bacterial expression systems, such as *E. coli*, provides non-glycosylated molecules. Further, a given preparation may include multiple differentially glycosylated species of the protein. Glycosyl groups can be removed through conventional methods, in particular those utilizing glycopeptidase. In general, glycosylated polypeptides of the invention can be incubated with a molar excess of glycopeptidase (Boehringer Mannheim).

Correspondingly, similar DNA constructs that encode various additions or substitutions of amino acid residues, or deletions of terminal or internal residues are encompassed by the invention. For example, N-glycosylation sites in the polypeptide extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. Appropriate substitutions, additions, or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Alternatively, the Ser or Thr can by replaced with another amino acid, such as Ala. Known procedures for inactivating N-glycosylation sites in proteins include those described in U.S. Pat. No. 5,071,972 and EP 276,846, hereby incorporated by reference.

In another example of variants, sequences encoding Cys residues that are not essential for biological activity can be altered to cause the Cys residues to be deleted or replaced with other amino acids, preventing formation of incorrect intramolecular disulfide bridges upon folding or renaturation.

Other variants are prepared by modification of adjacent dibasic amino acid residues, to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites.

Encompassed by the invention are oligomers or fusion proteins that contain the polypeptides, variants and fragments, described herein. Such oligomers may be in the form of covalently-linked or non-covalently-linked multimers, including dimers, trimers, or higher oligomers. In one aspect of the invention, the oligomers maintain similar ternary complex binding ability of the polypeptide components and provide therefor, bivalent, trivalent, etc., binding sites.

One embodiment of the invention is directed to oligomers comprising multiple polypeptides joined via covalent or non-covalent interactions between peptide moieties fused to the polypeptides. Such peptides may be peptide linkers (spacers), or peptides that have the property of promoting oligomerization. Leucine zippers and certain polypeptides derived from antibodies are among the peptides that can promote oligomerization of the polypeptides attached thereto, as described in more detail below.

As one alternative, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al. (*PNAS USA* 88:10535, 1991); Byrn et al. (*Nature* 344:677, 1990); and Hollenbaugh and Aruffo ("Construction of Immunoglobulin Fusion Proteins", in *Current Protocols in Immunology*, Suppl. 4, pages 10.19.1-10.19.11, 1992).

One fusion protein embodiment of the present invention is directed to a dimer comprising two fusion proteins created by fusing a polypeptide of the invention to an Fc polypeptide derived from an antibody. A gene fusion encoding the polypeptide/Fc fusion protein is inserted into an appropriate expression vector. Polypeptide/Fc fusion proteins are expressed in host cells transformed with the recombinant expression vector, and allowed to assemble much like antibody molecules, whereupon interchain disulfide bonds form between the Fc moieties to yield divalent molecules.

The term "Fc polypeptide" as used herein includes native and mutein forms of polypeptides made up of the Fc region of an antibody comprising any or all of the CH domains of the Fc region. Truncated forms of such polypeptides containing the hinge region that promotes dimerization are also included. Preferred polypeptides comprise an Fc polypeptide derived from a human IgG1 antibody.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., (*EMBO J.* 13:3992-4001, 1994) incorporated herein by reference. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

The above-described fusion proteins comprising Fc moieties (and oligomers formed therefrom) offer the advantage of facile purification by affinity chromatography over Protein A or Protein G columns.

In other embodiments, the polypeptides of the invention may be substituted for the variable portion of an antibody heavy or light chain. If fusion proteins are made with both heavy and light chains of an antibody, it is possible to form an oligomer with as many as four polypeptide extracellular regions.

Alternatively, the oligomer is a fusion protein comprising multiple polypeptides, with or without peptide linkers (spacer peptides). Among the suitable peptide linkers are those described in U.S. Pat. Nos. 4,751,180 and 4,935,233, which are hereby incorporated by reference. A DNA encoding a desired peptide linker may be inserted between, and in the same reading frame as, the DNA encoding a polypeptide of the invention, using any suitable conventional technique. For example, a chemically synthesized oligonucleotide encoding the linker may be ligated between the sequences. In particular embodiments, a fusion protein comprises from two to four polypeptides of this invention, separated by peptide linkers.

Another method for preparing the oligomers of the invention involves use of a leucine zipper. Leucine zipper domains are peptides that promote oligomerization of the proteins in which they are found. Leucine zippers were originally identified in several DNA-binding proteins (Landschulz et al., *Science* 240:1759, 1988), and have since been found in a variety of different proteins. Among the known leucine zippers are naturally occurring peptides and derivatives thereof that dimerize or trimerize.

The zipper domain (also referred to herein as an oligomerizing, or oligomer-forming, domain) comprises a repetitive heptad repeat, often with four or five leucine residues interspersed with other amino acids. Examples of zipper domains are those found in the yeast transcription factor GCN4 and a heat-stable DNA-binding protein found in rat liver (C/EBP; Landschulz et al., *Science* 243:1681, 1989). Two nuclear transforming proteins, fos and jun, also exhibit zipper domains, as does the gene product of the murine proto-oncogene, c-myc (Landschulz et al., *Science* 240: 1759, 1988). The products of the nuclear oncogenes fos and jun comprise zipper domains that preferentially form heterodimer (O'Shea et al., *Science* 245:646, 1989, Turner and Tjian, *Science* 243:1689, 1989). The zipper domain is necessary for biological activity (DNA binding) in these proteins.

The fusogenic proteins of several different viruses, including paramyxovirus, coronavirus, measles virus and many retroviruses, also possess zipper domains (Buckland and Wild, *Nature* 338:547, 1989; Britton, *Nature* 353:394, 1991; Delwart and Mosialos, *AIDS Research and Human Retroviruses* 6:703, 1990). The zipper domains in these fusogenic viral proteins are near the transmembrane region of the proteins; it has been suggested that the zipper domains could contribute to the oligomeric structure of the fusogenic proteins. Oligomerization of fusogenic viral proteins is involved in fusion pore formation (Spruce et al, *Proc. Natl. Acad. Sci.*U.S.A. 88:3523, 1991). Zipper domains have also been recently reported to play a role in oligomerization of heat-shock transcription factors (Rabindran et al., *Science* 259:230, 1993).

Examples of leucine zipper domains suitable for producing soluble oligomeric proteins are described in PCT application WO 94/10308, and the leucine zipper derived from lung surfactant protein D (SPD) described in Hoppe et al. (*FEBS Letters* 344:191, 1994), hereby incorporated by reference. The use of a modified leucine zipper that allows for stable trimerization of a heterologous protein fused thereto is described in Fanslow et al. (*Semin. Immunol.* 6:267-278, 1994). Recombinant fusion proteins comprising a soluble polypeptide fused to a leucine zipper peptide are expressed in suitable host cells, and the soluble oligomer that forms is recovered from the culture supernatant.

Certain leucine zipper moieties preferentially form trimers. One example is a leucine zipper derived from lung surfactant protein D (SPD), as described in Hoppe et al. (*FEBS Letters* 344:191, 1994) and in U.S. Pat. No. 5,716, 805, hereby incorporated by reference in their entirety. This lung SPD-derived leucine zipper peptide comprises the amino acid sequence Pro Asp Val Ala Ser Leu Arg Gln Gln Val Gln Ala Leu Gln Gly Gln Val Gln His Leu Gln Ala Ala Phe Ser Gln Tyr.

Another example of a leucine zipper that promotes trimerization is a peptide comprising the amino acid sequence Arg Met Lys Gln Ile Glu Asp Lys Ile Glu Glu Ile Leu Ser Lys Ile Tyr His Ile Glu Asn Glu Ile Ala Arg Ile Lys Lys Leu Ile Gly Glu Arg, as described in U.S. Pat. No. 5,716,805. In one alternative embodiment, an N-terminal Asp residue is added; in another, the peptide lacks the N-terminal Arg residue.

Fragments of the foregoing zipper peptides that retain the property of promoting oligomerization may be employed as well. Examples of such fragments include, but are not limited to, peptides lacking one or two of the N-terminal or C-terminal residues presented in the foregoing amino acid sequences. Leucine zippers may be derived from naturally occurring leucine zipper peptides, e.g., via conservative substitution(s) in the native amino acid sequence, wherein the peptide's ability to promote oligomerization is retained.

Other peptides derived from naturally occurring trimeric proteins may be employed in preparing trimeric IL-1R AcP of this invention. Alternatively, synthetic peptides that promote oligomerization may be employed. In particular embodiments, leucine residues in a leucine zipper moiety are replaced by isoleucine residues. Such peptides comprising isoleucine may be referred to as isoleucine zippers, but are encompassed by the term "leucine zippers" as employed herein.

Art recognized methods for expressing, isolating and purifying polypeptides are suitable for preparing and purifying polypeptides and polypeptide fragments of the present invention. In general, methods for producing polypeptides include the steps of culturing host cells that incorporate or a transfected with a an expression vector encoding the polypeptide, under conditions that promote expression of the polypeptide, then recovering the expressed polypeptides from the culture. The skilled artisan will recognize that the procedure for purifying the expressed polypeptides will vary according to such factors as the type of host cells employed, and whether the polypeptide is membrane-bound or a soluble form that is secreted from the host cell.

Vectors and host cells that incorporate polynucleotides of the present invention are within the scope of the present invention. DNA encoding a polypeptide or fragment of the invention, that is incorporated in vectors is operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired host cells, and a selection gene by which transformants are identified, are generally incorporated into the expression vector.

In addition, a polynucleotide encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide upon secretion of polypeptide from the cell.

The skilled artisan will also recognize that the position(s) at which the signal peptide is cleaved may differ from that predicted by computer program, and may vary according to such factors as the type of host cells employed in expressing a recombinant polypeptide. A protein preparation may include a mixture of protein molecules having different N-terminal amino acids, resulting from cleavage of the signal peptide at more than one site. Thus, particular embodiments of mature proteins provided herein include, but are not limited to, proteins having the N-terminal residue at the predicted cleavage of the signal peptide, amino acid 17-18 of SEQ ID NO:2 and amino acid 17-18 of SEQ ID NO:4 as the N-terminal or C-terminal amino acid.

Suitable host cells for expressing polypeptides include prokaryotes, yeast or higher eukaryotic cells. Mammalian or insect cells are generally preferred for use as host cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce polypeptides using RNAs derived from DNA constructs disclosed herein.

Prokaryotes include gram-negative or gram-positive organisms. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, a polypeptide may include an N-terminal methionine residue to facilitate expression of the recombinant polypeptide in the prokaryotic host cell. The N-terminal Met may be cleaved from the expressed recombinant polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratcny Manual*, Cold Spring Harbor Laboratory, p. 412, 1982). A particularly useful prokaryotic host cell expression system employs a phage $\lambda P_L$ promoter and a cI857ts thermolabile repressor sequence. Plasmid vectors available from the American Type Culture Collection which incorporate derivatives of The $\lambda P_L$ promoter include plasmid pHUB2 (resident in *E. coli* strain JMB9, ATCC 37092) and pPLc28 (resident in *E. coli* RR1, ATCC 53082).

IL-1R AcP encoding DNA of the present invention may be cloned in-frame into the multiple cloning site of an ordinary bacterial expression vector. Ideally the vector would contain an inducible promoter upstream of the cloning site, such that addition of an inducer leads to high-level production of the recombinant protein at a time of the investigator's choosing. For some proteins, expression levels may be boosted by incorporation of codons encoding a fusion partner (such as hexahistidine) between the promoter and the gene of interest. The resulting "expression plasmid" may be propagated in a variety of strains of *E. coli*.

For expression of the recombinant protein, the bacterial cells are propagated in growth medium until reaching a pre-determined optical density. Expression of the recombinant protein is then induced, e.g. by addition of IPTG (isopropyl.b-D-thiogalactopyranoside), which activates expression of proteins from plasmids containing a lac operator/promoter. After induction (typically for 1-4 hours), the cells are harvested by pelleting in a centrifuge, e.g. at 5,000 ×G for 20 minutes at 40° C.

For recovery of the expressed protein, the pelleted cells may be resuspended in ten volumes of 50 mM Tris-HCl (pH 8)/1 M NaCl and then passed two or three times through a French press. Most highly expressed recombinant proteins form insoluble aggregates known as inclusion bodies. Inclusion bodies can be purified away from the soluble proteins by pelleting in a centrifuge at 5,000 ×G for 20 minutes, 4° C. The inclusion body pellet is washed with 50 mM Tris-HCl (pH 8)/1% Triton X-100 and then dissolved in 50 mM Tris-HCl (pH 8)/8 M urea/0.1 M DTTf. Any material that cannot be dissolved is removed by centrifugation (10,000 ×G for 20 minutes, 20° C.). The protein of interest will, in most cases, be the most abundant protein in the resulting clarified supernatant. This protein may be "refolded" into the active conformation by dialysis against 50 mM Tris-HCl (pH 8)/5 mM $CaCl_2$/5 mM $Zn(OAc)_2$/1 mM GSSG/0.1 mM GSH. After refolding, purification can be cried out by a variety of chromatographic methods, such as ion exchange or gel filtration. In some protocols, initial purification may be carried out before refolding. As an example, hexahistidine-tagged fusion proteins may be partially purified on immobilized Nickel.

While the preceding purification and refolding procedure assumes that the protein is best recovered from inclusion bodies, those skilled in the art of protein purification will appreciate that many recombinant proteins are best purified out of the soluble fraction of cell lysates. In these cases, refolding is often not required, and purification by standard chromatographic methods can be carried out directly.

Alternatively, the polypeptides may be expressed in yeast host cells, preferably from the *Saccharomyces* genus (e.g., *S cerevisiae*). Other genera of yeast, such as *Pichia* or *Kluyveromyces*, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Blot. Chem.* 255:2073, 1980) or other glycolytic enzymes (Hess et al., *J. Adv. Enzyme .Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glueose-6-phosphate isomerase, 3-phosphoglycerate mnutase, pyruvate kinase, triosephospliate isomerase, phospho-glucose isomerase, and glucokinase. Other suitable vectors and promoters for use in yeast expression are further described in Hitzeman, EPA-73,657. Another alternative is the glucose-repressible ADH2 promoter described by Russell et al. (*J. Biol. Chem.* 258:2674, 1982) and Beier et al. (*Nature* 3 00:724, 1982). Shuttle vectors replicable in both yeast and *E. coli* may be constructed by inserting DNA sequences from pBR322 for selection and replication in *E. coli* (Amp$_T$ gene and origin of replication) into the above-described yeast vectors.

The yeast α-factor leader seqaence may be employed to direct secretion of the polypeptide. The α-factor leader sequence is often inserted between the promoter sequence and the structural gene sequence. See, e.g., Kurjan et at, *Cell* 30:933, 1982 and Bitter et al., *Proc. Natl. Acad. Sci. USA* 81:5330, 1984. Other leader sequences suitable for facilitating secretion of recombinant polypeptides from yeast hosts are latown to those of skill in the art. A leader sequence may be modified near its 3' end to contain one or more restriction sites. Tbis will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 mg/ml adenine and 20 mg/ml uracil.

Yeast host cells transformed by vectors containing an ADH2 promoter sequence may be grown for inducing expression in a "rich" medium. An example of a rich medium is one consisting of 1% yeast extract, 2% peptone, and 1% glucose supplemented with 80 mg/ml adenine and 80 mg/ml uracil. Derepression of the ADH2 promoter occurs when glucose is exhausted from the medium.

Mammalian or insect host cell culture systems also may be employed to express recombinant polypeptides. Bacculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by McMahan et al. (*EMBO J.* 10: 2821, 1991).

Established methods for introducing DNA into mammalian cells have been described (Kaufman, R. J., *Large Scale Mammalian Cell Culture*, 1990, pp. 15-69). Additional protocols using commercially available reagents, such as Lipofectamine lipid reagent (Gibco/BRL) or Lipofectamine-Plus lipid reagent, can be used to transfect cells (Felgner et al., *Proc. Natl. Acad. Sci. USA* 84:7413-7417, 1987). In addition, electroporation can be used to transfect mammalian cells using conventional procedures, such as those in Sambrook et al. (*Molecular Cloning: A Laboratory Manual*, 2 ed. Vol. 1-3, Cold Spring Harbor Laboratory Press, 1989). Selection of stable transformants can be performed using methods known in the art, such as, for example, resistance to cytotoxic drugs. Kaufman et al., *Meth. in Enzymology* 185:487-511, 1990, describes several selection schemes, such as dihydrofolate reductase (DHFR) resistance. A suitable host strain for DHFR selection can be CHO strain DX-B11, which is deficient in DHFR (Urlaub and Chasin, *Proc. Natl. Acad. Sci. USA* 77:4216-4220, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., *Nature* 273:113, 1978; Kaufman, *Meth. in Enzymology*, 1990). Smaller or larger SV40 fragments can also be used, provided the approximately 250 bp sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., *Animal Cell Technology*, 1997, pp.529-534 and PCT Application WO 97/25420) and the tripartite leader (TPL) and VA gene RNAs from Adenovirus 2 (Gingeras et al., *J. Biol. Chem.* 257:13475-13491, 1982). The internal ribosome entry site (IRES) sequences of viral origin allows dicistronic mRNAs to be translated efficiently (Oh and Sarnow, *Current Opinion in Genetics and Development* 3:295-300, 1993; Ramesh et al., *Nucleic Acids Research* 24:2697-2700, 1996). Expression of a heterologous cDNA as part of a dicistronic mRNA followed by the gene for a selectable marker (e.g. DHFR) has been shown to improve transfectability of the host and expression of the heterologous cDNA (Kaufman, *Meth. in Enzymology*, 1990). Exemplary expression vectors that employ dicistronic mRNAs are pTR-DC/GFP described by Mosser et al., *Biotechniques* 22:150-161, 1997, and p2A5I described by Morris et al., *Animal Cell Technology*, 1997, pp. 529-534.

A useful high expression vector, pCAVNOT, has been described by Mosley et al., *Cell* 59:335-348, 1989. Other expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984, has been deposited as ATCC 39890. Additional useful mammalian expression vectors are described in EP-A-0367566, and in WO 91/18982, incorporated by reference herein. In yet another alternative, the vectors can be derived from retroviruses.

Additional useful expression vectors, pFLAG® and pDC311, can also be used. FLAG® technology is centered on the fusion of a low molecular weight (1 kD), hydrophilic, FLAG® marker peptide to the N-terminus of a recombinant protein expressed by pFLAG® expression vectors. pDC311 is another specialized vector used for expressing proteins in CHO cells. pDC311 is characterized by a bicistronic sequence containing the gene of interest and a dihydrofolate reductase (DHFR) gene with an internal ribosome binding site for DHFR translation, an expression augmenting sequence element (EASE), the human CMV promoter, a tripartite leader sequence, and a polyadenylation site.

Regarding signal peptides that may be employed, the native signal peptide may be replaced by a heterologous signal peptide or leader sequence, if desired. The choice of signal peptide or leader may depend on factors such as the type of host cells in which the recombinant polypeptide is to be produced. To illustrate, examples of heterologous signal peptides that are functional in mammalian host cells include the signal sequence for interleukin-7 (IL-7) described in U.S. Pat. No. 4,965,195; the signal sequence for interleukin-2 receptor described in Cosman et al., *Nature* 312:768 (1984); the interleukin-4 receptor signal peptide described in EP 367,566; the type I interleukin-1 receptor signal peptide described in U.S. Pat. No. 4,968,607; and the type II interleukin-1 receptor signal peptide described in EP 460,846.

The invention also includes methods of isolating and purifying the polypeptides and fragments thereof. An isolated and purified polypeptide according to the invention can be produced by recombinant expression systems as described above or purified from naturally occurring cells. Polypeptides can be substantially purified, as indicated by a single protein band upon analysis by SDS-polyacrylamide gel electrophoresis (SDS-PAGE).

The expression "isolated and purified" as used herein means that a IL-1R AcP polypeptide of this invention is essentially free of association with other, proteins, or polypeptides, for example, as a purification product of recombinant host cell culture or as a purified product from a non-recombinant source. The term "substantially purified" as used herein refers to a mixture that contains a polypeptide and is essentially free of association with other DNA, proteins, or polypeptides, but for the presence of known DNA or proteins that can be removed using a specific antibody, and which substantially purified proteins retain biological activity. The term "purified polypeptide" refers to either the "isolated and purified" form of the polypeptide or the "substantially purified" form of the polypeptide, as both are described herein.

The term "biologically active" as it refers to a IL-1R AcP polypeptide or a IL-1R AcP polypeptide fragment of this invention, means that the polypeptide, or polypeptide fragment, is capable of associating with an IL-1 receptor or an IL-1 receptor family member, or that the IL-1R AcP polypeptide or fragment interacts with intracellular signal transduction proteins.

In one preferred embodiment, the purification of recombinant polypeptides or fragments can be accomplished using fusions of polypeptides or fragments of the invention to another polypeptide to aid in the purification of polypeptides or fragments of the invention. Such fusion partners can include the poly-His or other antigenic identification peptides described above as well as the Fc moieties described previously.

With respect to any type of host cell, procedures for purifying a recombinant polypeptide or fragment will vary according to such factors as the type of host cells employed and whether or not the recombinant polypeptide or fragment is secreted into the culture medium. In general, the recombinant polypeptide or polypeptide fragment can be isolated from the host cells if not secreted, or from the medium or supernatant if soluble and secreted, followed by one or more concentration, salting-out, ion exchange, hydrophobic interaction, affinity purification or size exclusion chromatography steps. As to specific ways to accomplish these steps, the culture medium first can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The anion exchange matrices may be acrylamide, agarose, dextran, cellulose or other types commonly employed in protein purification. Alternatively, a cation exchange resin can be used for purification, in which case suitable cation exchangers are insoluble matrices having sulfopropyl or carboxymethyl funcitonal groups. Other purification techniques useful in the processes of this invention include chromatofocusing procedures or hydrophobic interaction chromatography or affinity chromatography with a matrix which selectively binds the recombinant protein. Examples of such resins employed are lectin columns, dye columns, and metal-chelating columns. Finally, one or more reversed-phase high performance liquid chromatography (RP-HPLC) steps employing hydrophobic RP-HPLC media, (e.g., silica gel or polymer resin having pendant methyl, octyl, octyldecyl or other aliphatic groups) can be employed to further purify the polypeptides. Some or all of the foregoing purification steps, in various combinations, are well known and can be employed to provide an isolated and purified recombinant protein.

Recombinant protein produced in bacterial culture is usually isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

It is also possible to utilize an affinity column comprising a polypeptide-binding protein of the invention, such as a monoclonal antibody generated against polypeptides of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention.

In this aspect of the invention, polypeptide-binding proteins, such as the anti-polypeptide antibodies of the invention or other proteins that may interact with the polypeptide of the invention, can be bound to a solid phase support such as a column chromatography matrix or a similar substrate suitable for identifying, separating, or purifying cells that express polypeptides of the invention on their surface. Adherence of polypeptide-binding proteins of the invention to a solid phase contacting surface can be accomplished by any means, for example, magnetic microspheres can be coated with these polypeptide-binding proteins and held in the incubation vessel through a magnetic field. Suspensions of cell mixtures are contacted with the solid phase that has such polypeptide-binding proteins thereon. Cells having polypeptides of the invention on their surface bind to the fixed polypeptide-binding protein and unbound cells then are washed away. This affinity-binding method is useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner.

Alternatively, mixtures of cells suspected of containing polypeptide-expressing cells of the invention first can be incubated with a biotinylated polypeptide-binding protein of the invention. Incubation periods are typically at least one hour in duration to ensure sufficient binding to polypeptides of the invention. The resulting mixture then is passed through a column packed with avidin-coated beads, whereby the high affinity of biotin for avidin provides the binding of the polypeptide-binding cells to the beads. Use of avidin-coated beads is known in the art. See Berenson, et al. *J. Cell. Biochem.*, 10D:239 (1986). Wash of unbound material and the release of the bound cells is performed using conventional methods.

In the methods described above, suitable IL-1R AcP binding polypeptides are anti-IL-1R AcP antibodies and other proteins that are capable of high-affinity binding of the expressed polypeptide.

The desired degree of purity depends on the intended use of the protein. A relatively high degree of purity is desired when the polypeptide is to be administered in vivo, for example. In such a case, the polypeptides are purified such that no protein bands corresponding to other proteins are detectable upon analysis by SDS-polyacrylamide gel electrophoresis (SDS-PAGE). It will be recognized by one skilled in the pertinent field that multiple bands corresponding to the polypeptide may be visualized by SDS-PAGE, due to differential glycosylation, differential post-translational processing, and the like. Most preferably, the polypeptide of the invention is purified to substantial homogeneity, as indicated by a single protein band upon analysis by SDS-PAGE. The protein band may be visualized by silver staining, Coomassie blue staining, or (if the protein is radiolabeled) by autoradiography.

The purified polypeptides of the invention (including proteins, polypeptides, fragments, variants, oligomers, and other forms) may be tested for the ability to bind a IL-1R and/or a IL-1R family member or its ability to form a ternary complex with IL-1R and IL-1 in any suitable assay, such as a conventional binding assay. To illustrate, the sample polypeptide may be labeled with a detectable reagent (e.g., a radionuclide, chromophore, enzyme that catalyzes a colorimetric or fluorometric reaction, and the like). The labeled polypeptide is contacted with cells expressing an IL-1R and/or IL-1. The cells then are washed to remove unbound labeled polypeptide, and the presence of cell-bound label is determined by a suitable technique, chosen according to the nature of the label.

One example of a binding assay procedure is as follows. A recombinant expression vector containing IL-1R cDNA is constructed, for example, fusing the extracellular domain of an IL-1R to the IgG-I Fc (mutein form) as previously described for OX40/Fc (Baum et al., EMBO J. 13:3992-4001, 1994). CV1-EBNA-1 cells in 10 $cm^2$ dishes are transfected with the recombinant expression vector. CV-1/EBNA-1 cells (ATCC CRL 10478) constitutively express EBV nuclear antigen-1 driven from the CMV immediate-early enhancer/promoter. CV1-EBNA-1 was derived from the African Green Monkey kidney cell line CV-1 (ATCC CCL 70), as described by McMahan et al. (*EMBO J.* 10:2821, 1991).

The transfected cells are cultured for 24 hours, and the cells in each dish then are split into a 24-well plate. After culturing an additional 48 hours, the transfected cells (about $4 \times 10^4$ cells/well) are washed with BM-NFDM, which is binding medium (RPMI 1640 containing 25 mg/ml bovine serum albumin, 2 mg/ml sodium azide, 20 mM Hepes pH 72) to which 50 mg/ml nonfat dry milk has been added. The cells then are incubated for 1 hour at 37° C. with various concentrations of, for example, a soluble polypeptide/Fc fusion protein made as set forth above. Cells then are washed and incubated with a constant saturating concentration of a $^{125}$I-mouse anti-human IgG in binding medium, with gentle agitation for 1 hour at 37° C. After extensive washing, cells are released via trypsinization.

The mouse anti-human IgG employed above is directed against the Fc region of human IgG and can be obtained from Jackson Immunoresearch Laboratories, Inc., West Grove, Pa. The antibody is radioiodinated using the standard chloramine-T method. The antibody will bind to the Fc portion of any polypeptide/Fc protein that has bound to the cells. In all assays, non-specific binding of $^{125}$I-antibody is assayed in the absence of the Fc fusion protein, as well as in the presence of the Fc fusion protein and a 200-fold molar excess of unlabeled mouse anti-human IgG antibody.

Cell-bound $^{125}$I-antibody is quantified on a Packard Autogamma counter. Affinity calculations (Scatchard, *Ann. N.Y. Acad. Sci.* 51:660, 1949) are generated on RS/1 (BBN Software, Boston, Mass.) run on a Microvax computer.

Another type of suitable binding assay is a competitive binding assay. To illustrate, biological activity of a variant may be determined by assaying for the variant's ability to compete with the native protein for binding to an IL-1 receptor or IL-1 receptor family member.

Competitive binding assays can be performed by conventional methodology. Reagents that may be employed in competitive binding assays include a radiolabeled IL-1R, IL-1 and intact cells expressing IL-1R AcP(endogenous or recombinant) on the cell surface. For example, a radiolabeled soluble IL-1R AcP fragment of the present invention can be used to compete with a soluble IL-1R AcP variant for binding to cell surface (binding partner). Instead of intact cells, one could substitute a soluble IL-1R/Fc fusion protein bound to a solid phase through the interaction of Protein A or Protein G (on the solid phase) with the Fc moiety. Chromatography columns that contain Protein A and Protein G include those available from Pharmacia Biotech, Inc., Piscataway, N.J.

Another type of competitive binding assay utilizes radiolabeled IL-1R such as a soluble an Fc fusion protein, and intact cells expressing IL-1R AcP of this invention. Qualitative results can be obtained by competitive autoradiographic plate binding assays, while Scatchard plots (Scatchard, *Ann. N.Y. Acad. Sci.* 51:660, 1949) may be utilized to generate quantitative results.

In addition to being used to express polypeptides as described above, the nucleic acids of the invention, including DNA, and oligonucleotides thereof can be used:
  as probes to identify polynucleotides encoding proteins having IL-1R AcP activity;
  as single-stranded sense or antisense oligonucleotides, to inhibit expression of polypeptide encoded by the IL-1R AcP polynucleotides of this invention;

Fragment that are useful as probes or primers generally include at least about 17 contiguous nucleotides of a polynucleotide that encodes a fragment of the polypeptide of SEQ ID NO:2 or SEQ ID NO:4. In other embodiments, a fragment comprises at least 30, or at least 60, contiguous nucleotides of an similarly encoding polypeptide.

Because homologs of SEQ ID NO:1 from other mammalian species are contemplated herein, probes based on the DNA sequence of SEQ ID NO:1 may be used to screen cDNA libraries derived from other mammalian species, using conventional cross-species hybridization techniques.

Using knowledge of the genetic code in combination with the amino acid sequences set forth above, sets of degenerate oligonucleotides can be prepared. Such oligonucleotides are useful as primers, e.g., in polymerase chain reactions (PCR), whereby DNA fragments are isolated and amplified.

Other useful fragments of the polynucleotides of this invention include antisense or sense oligonucleotides comprising a single-stranded nucleic acid sequence (either RNA or DNA) capable of binding to target mRNA (sense) or DNA (antisense). Antisense or sense oligonucleotides, according to the present invention, include polynucleotide fragments of SEQ ID NO:1 and/or SEQ ID NO:3. Such fragments generally comprises at least about 14 nucleotides, preferably from about 14 to about 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acids results in the formation of duplexes that block or inhibit protein expression by one of several means, including enhanced degradation of the mRNA by RNAseH, inhibition of splicing, premature termination of transcription or translation, or by other means. The antisense oligonucleotides thus may be used to block expression of proteins. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, lipofection, $CaPO_4$-mediated DNA transfection, electroporation, or by using gene transfer vectors such as Epstein-Barr virus.

Sense or antisense oligonucleotides are preferably introduced into a cell containing the target polynucleotides by insertion of the sense or antisense oligonucleotide into a suitable retroviral vector, then contacting the cell with the retrovirus vector containing the inserted sequence, either in vivo or ex vivo. Suitable retroviral vectors include, but are not limited to, the murine retrovirus M-MuLV, N2 (a retrovirus derived from M-MuLV), or the double copy vectors designated DCT5A, DCT5B and DCT5C (see PCT Application US 90/02656).

Sense or antisense oligonucleotides also may be introduced into a cell containing the target nucleotide by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase to a monoclonal antibody targeted to a specific cell type.

Polypeptides of the present invention have a variety of uses including, but not limited to: therapeutic agents for diseases mediated by IL-1 family members, models for rational drug design, targets in screening assays directed to the discovery of inhibitors or enhancers of IL-1R AcP signaling pathways, and antigens in antibody preparation. As demonstrated in Example 1, IL-1R AcP polypeptides of this invention are expressed in the brain and central nervous system tissue. Accordingly, Il-1R AcP polypeptides, IL-1R AcP polypeptides fragments, agonists and antagonists of IL-1R AcP of this invention, agonistic and antagonistic antibodies to IL-1R AcP are useful as therapeutic agents in the treatment and prevention of diseases associated with brain and CNS tissue.

The IL-1R AcP polypeptide and active fragments of the IL-1R AcP polypeptide of this invention are particularly useful as targets in assays designed to screen for and discover inhibitors or enhancers of signaling pathways of IL-1 and IL-1receptor family members. IL-1 family members that bind to an IL-1 receptor or IL-1 receptor family member interact with an IL-1R AcP of this invention to initiate a signaling response that includes the association or interaction of the cytoplasmic domains of the IL-1 receptor or receptor family member and IL-1R AcP with MyD88 and signaling through IRAK-1, IRAK-2, IRAK-M, or TRAF6. Thus, the disclosed IL-1R AcP polypeptides find utility in in vitro screening assays directed toward the discovery of agents that antagonize of agonize the interaction of the IL-1R AcP cytoplasmic domain with MyD88, IRAK-1, IRAK-2, IRAK-M and TRAF6. Similarly, the disclosed IL-1R AcP polypeptides find utility in screening assays directed toward the discovery of agents that interrupt or enhance the association of IL-1 family members and/or IL-1 receptor family member or IL-1 receptor.

Advantageously, inhibitors that specifically disrupt, for example, the association of IL-1R AcP with one or more IL-1 family member or IL-1 receptor family members, or inhibitors that disrupt intracellular signaling factors are not likely to effect signaling from other cytokine receptors and thus can be useful therapeutic agents. Since, in some situations, as described above, the IL-1R AcP of this invention may antagonize the cellular responses to IL-1, or IL-1 family members, agonists of the inhibitory capacity of the IL-1R AcP of this invention are useful immunosuppressants or anti-inflammatory agents. Conversely, therapeutic agents that suppress or inhibit a negative regulatory or inhibitory function of IL-1R AcP are useful immuno upregulators, e.g. provide increased immune activity and enhance the effects of one or more IL-1 family members in individuals with depressed function. In situations where IL-1R AcP of this invention acts in a pro-inflammatory capacity, by activating NF-κB, therapeutic agents that are antagonists of IL-1R AcP of this invention are useful as an anti-inflammatory agent. Such agents are useful to treat inflammatory conditions described herein. Accordingly, IL-1 family member immunoregulators, that are discovered using the disclosed IL-1R AcP polypeptides are useful as therapeutics in the treatment of diseases mediated by IL-1 family members as discussed below.

Suitable screening methods of this invention include methods that assay test compounds for their ability to modulate IL-1R AcP interactions with intracellular signaling factors and their ability to modulate activities mediated by such IL-1R AcP interactions. To this end, the present invention includes compounds that modulate IL-1R AcP interactions and that are identified by the screening methods of the present invention. In general, screening methods of this invention involve allowing the disclosed IL-1R AcP polypeptide or IL-1R AcP polypeptide fragment, e.g. the cytoplasmic domain or fragment thereof, that is known to bind or interact with an intracellular signaling factor, e.g. MyD88, to interact with the factor under conditions in which the IL-1R AcP polypeptide is known to bind or interact with the factor. The IL-1R AcP interaction is allowed to occur in the presence of a test compound or the test compound is allowed to contact the IL-1R AcP subsequent to their interaction. By observing the effect that the test compound has on the known binding characteristics of the IL-1R AcP polypeptide or fragment, test compounds that enhance IL-1R AcP interactions can be determined and test compounds that inhibit IL-1R AcP interactions can be identified.

Typical test compounds are small molecules or peptides and may be part of extensive small molecule libraries developed for use in screening methods. IL-1R AcP polypeptides that may be used in screening methods include the full length herein disclosed IL-1R AcP, the cytoplasmic domain of the disclosed IL-1R AcP polypeptide, fragments of the cytoplasmic domain that interact with signal transduction factors, and polypeptide mutants or analogs or variants that interact signal transduction factors. Particularly useful signal transduction factors include MyD88 and down stream factors such as IRAK-1, IRAK-2, IRAK-M and TRAF6. The signal transduction factors may be recombinantly prepared and used directly in cells or isolated. Similarly, native signal transduction factors can be used in cells or isolated and used in in vitro assays.

Specific screening methods are known in the art and many are extensively incorporated in high throughput test systems so that large numbers of test compounds can be screened within a short amount of time. Suitable screening methods can be performed in a variety of formats including, but not limited to, binding assay screens, functional assay screens and cell based screens. By observing the affect that test compounds have on the signal transduction factor interaction with IL-1R AcP in binding assays, on activity mediated by IL-1 family members in functional tests and in cell based screens, compounds that are potential therapeutics because they can modulate the interaction of IL-1R AcP with signal transduction factors and IL-1 family members and thus the effects of are identified.

Binding assays and their use in screening methodologies are known in the art. For example, U.S. Pat. No. 5,767,244 (incorporated herein by reference) describes methods useful for screening compounds that are active at the level of a TRAF6 modulatable cellular function. In particular, binding assays can be used to screen for test compounds that are capable of modulating binding functions. Suitable assays include standard protein-protein interaction tests that demonstrate the presence or absence of protein-protein interactions and measure binding affinities. Typically, such binding assays involve incubating a test mixture under conditions in which the desired signal transduction factor and polypeptide, polypeptide fragment or polypeptide analog binds with a known binding affinity. Forms of IL-1R AcP of this invention that are particularly useful in screening for modulators of the interaction include the full length IL-1R AcP cytoplasmic domain of SEQ ID NO:2 and SEQ ID NO:4 as disclosed above and fragments of the cytoplasmic domain that are capable of interacting with or modulating the relevant signal transduction factor.

Protein-protein interactions can be observed and measured in binding assays using a variety of detection methodologies that include, but are not limited to, surface plasmon resonance (Biacore), radioimmune based assays, and fluorescence polarization binding assays. When performed in the presence of a test compound, the ability of the test compound to modulate (e.g. inhibit or enhance) the protein-protein binding affinity is measured. Test compounds shown to modulate IL-1R AcP and IL-1 family member interactions may be therapeutic agents for diseases associated with IL-1 family members.

The disclosed IL-1R AcP polypeptide, fragments (including the cytoplasmic domain fragments identified above), mutants and analogs are also useful in cell based assay methods that screen for test compounds which are inhibitors or modulators of the IL-1R AcP/signal transduction factor interactions. Advantageously, cell based assays are mechanism based and can be designed to assay test compounds for their cell membrane permeability characteristics; their ability to modulate relevant interactions; their ability to selectivity modulate a specific activity mediated by IL-1 family members; and their cell toxicity characteristics. A number of cell based methods are known in the art. Many of the assays are based upon a yeast two-hybrid assay or mammalian two-hybrid assay. (See White, *Proc. Natl. Acad. Sci.* USA 93:10001-10003, 1996). Yeast two hybrid assays as they relate to selecting small molecule inhibitors of protein-protein interactions are described in Huang et al. *Proc. Natl. Acad. Sci* 94:13396-13401, 1997. Typically, these assays involve expressing proteins (e.g. the disclosed IL-1R AcP polypeptides or suitable fragments as disclosed herein and a signal transduction factor) whose interaction triggers a reporter gene. Test compounds that are cell permeable can be identified for their ability to modulate the IL-1R AcP/signal transduction factor interaction as noted by a difference in the reporter gene triggering as compared with the reporter gene triggering in the absence of the test compound.

Additional assays that are useful for discovering modulators of IL-1R AcP interactions include in vivo functional assays. For example, test compounds can be screened for their ability to inhibit cell functions that are linked to diseases mediated by IL-1 family members. Such cell functions include, but are not limited to, activation or inhibition of cell specific responses, proliferation, and inflammatory reactions based on changes in signal transduction, activating vascular endothelial cells and lymphocytes, induction of inflammatory cytokines, acute phase proteins, hematopoiesis, fever, bone resorption, prostaglandins, metalloproteinases, and adhesion molecules.

In addition to screening methodologies, IL-1R AcP polypeptides disclosed herein are useful for structure-based design of inhibitors of pathways and diseases mediated by IL-1 family members. Such structure-based design is also known as "rational drug design." The IL-1R AcP polypeptides, IL-1R AcP complexes with IL-1 receptor family members can be three-dimensionally analyzed by, for example, X-ray crystallography, nuclear magnetic resonance or homology modeling, all of which are well-known methods. The use of IL-1R AcP structural information in molecular modeling software systems to assist in inhibitor design is also encompassed by the invention. Such computer-assisted modeling and drug design may utilize information such as chemical conformational analysis, electrostatic potential of the molecules, protein folding, etc. A particular method of the invention comprises analyzing the three dimensional structure of IL-1R AcP for likely binding sites, extracellular or intracellular, of substrates, synthesizing a new molecule that incorporates a predictive reactive site, and assaying the new molecule as described above.

Delivery Agents

The polypeptides described herein can be used to deliver diagnostic or therapeutic agents to such cells or cell types found to express molecules with which the polypeptides complex or bind in in vitro or in vivo procedures. Therefore, the polypeptides described herein can be attached to a toxin to bind to cells that express IL-1 receptor family members to which they bind and specifically kill these cells. The methodology can be similar to the successful use of an anti-CD72 immunotoxin to treat therapy-refractory B-lineage acute lymphoblastic leukemia in SCID mice (Meyers et al., *Leuk. and Lymph.* 18:119-122).

Detectable (diagnostic) and therapeutic agents that may be attached to a polypeptide include, but are not limited to, toxins, other cytotoxic agents, drugs, radionuclides, chromophores, enzymes that catalyze a colorimetric or fluorometric reaction, and the like, with the particular agent being chosen according to the intended application. Among the toxins are ricin, abrin, diphtheria toxin, *Pseudomonas aeruginosa* exotoxin A, ribosomal inactivating proteins, mycotoxins such as trichothecenes, and derivatives and fragments (e.g., single chains) thereof. Radionuclides suitable for diagnostic use include, but are not limited to, $^{123}$I, $^{131}$I, $^{99m}$Tc, $^{111}$In, and $^{76}$Br. Examples of radionuclides suitable for therapeutic use are $^{131}$I, $^{211}$At, $^{77}$Br, $^{186}$Re, $^{188}$Re, $^{212}$Pb, $^{212}$Bi, $^{109}$Pd, $^{64}$Cu, and $^{67}$Cu.

Such agents may be attached to the polypeptide by any suitable conventional procedure. One such procedure involves reacting reactive functional groups on an agent with functional groups on one or more polypeptide amino acid side chains. If suitable functional groups are not present or not present in the desired location, the protein or agent may be derivatized to generate or attach a desired reactive functional group. The derivatization may involve attachment of one of the bifunctional coupling reagents available for attaching various molecules to proteins (Pierce Chemical Company, Rockford, Ill.). A number of techniques for radio-labeling proteins are known. Radionuclide metals may be attached to polypeptides by using a suitable bifunctional chelating agent, for example. The foregoing described procedures can be application to preparing conjugates of polypeptide of this invention and a suitable diagnostic or therapeutic agent (preferably covalently linked). Such conjugates are administered or otherwise employed in an amount appropriate for the particular application.

Further embodiments of the present invention include therapeutic uses of the disclosed IL-1R AcP polypeptides and polypeptide fragments. Such therapeutic uses generally involve the inhibition of the action of IL-1 or IL-1 homologues that play a central role in protection against infection and immune inflammatory responses. IL-1 is involved in cellular signal transduction, activating vascular endothelial cells and lymphocytes, induction of inflammatory cytokines, acute phase proteins, hematopoiesis, fever, bone resorption, prostaglandins, metalloproteinases, and adhesion molecules. IL-1R AcP described herein is involved in the functions noted above as well as modulating inflammatory responses and therefore perhaps be involved in the negative regulation of and the causation and maintenance of inflammatory and/or autoimmune diseases such as rheumatoid arthritis, inflammatory bowel disease, and psoriasis. As such, alterations in the expression and/or activation of IL-1R AcP can have profound effects on a plethora of cellular processes, including, but not limited to, activation or inhibition of cell specific responses, proliferation, and inflammatory reactions based on changes in signal transduction.

For many IL-1 family members, the cellular signaling involves a molecular activation cascade, during which a receptor propagates a ligand-receptor mediated signal by specifically activating intracellular kinases which phosphorylate target substrates, resulting in the activation of the transcription factors NFκB and AP1, the protein kinases Jun N-terminal kinase and p38 map kinase, the enzymes COX-2 leading to prostaglandin production and iNOS leading to nitric oxide production, and inflammation in general.

Thus, isolated IL-1R AcP polypeptides described herein, which interact with at least one IL-1 family member and IL-1 receptor family member, can be useful as therapeutic agents. In situations where an IL-1R AcP of this invention has an inhibitory role, polypeptide and polypeptide fragments of this invention can be useful in inhibiting signaling. In cases in which IL-1R AcP of this invention is not a negative regulator, soluble polypeptides can interact with relevant IL-1 receptor family members or IL-1 family members, and inhibit the activation of cells through cell-associated IL-1R AcP. Furthermore, the cytoplasmic domain or fragments thereof that are capable of binding signal transduction factors may be engineered for introduction into the intracellular environment where they bind to signal transduction factors and inhibit signaling through cell-associated IL-1R AcP.

Specific medical conditions and diseases that are treatable or preventable with the IL-1R AcP polypeptides of this invention include coeliac disease, Crohn's disease; ulcerative colitis; idiopathic gastroparesis; pancreatitis, including chronic pancreatitis; inflammatory bowel disease and ulcers, including gastric and duodenal ulcers.

As described above and shown in Example 1, IL-1R AcP of this invention is expressed in brain/CNS tissue. Thus, modulators of IL-1R AcP activity that are described above are useful in treating diseases associated with the central nervous system, the head, the spinal chord and brain, including head and spinal chord injuries and subdural hematoma due to trauma to the head. The therapeutic agents described herein and discovered through screening activities can be used to treat cranial neurologic damage and to prevent and treat cervicogenic headaches and to treat neurological side effects associated with brain irradiation.

Therapeutic agents that are modulators of IL-1R AcP of this invention can also be used to treat or prevent primary amyloidosis. In addition, secondary amyloidosis that is characteristic of various conditions also are treatable modulators of IL-1R AcP of this invention. Such conditions include: Alzheimer's disease, secondary reactive amyloidosis; Down's syndrome; and dialysis-associated amyloidosis. Various other medical disorders treatable with the therapeutic agents that are modulators of IL-1R AcP include; multiple sclerosis; Behcet's syndrome; Sjogren's syndrome; autoimmune hemolytic anemia; beta thalassemia; amyotrophic lateral sclerosis (Lou Gehrig's Disease); Parkinson's disease; and tenosynovitis of unknown cause, as well as various autoimmune disorders or diseases associated with hereditary deficiencies, including x-linked mental retardation.

Further uses for the therapeutic agents that are modulators of the IL-1R AcP described here include treating central nervous system (CNS) injuries, including the effects of neurotoxic neurotransmitters discharged during excitation of inflammation in the central nervous system and to inhibit or prevent the development of glial scars at sites of central nervous system injury. In connection with central nervous system medical conditions, the modulators of IL-1R AcP of this invention are useful in treating temporal lobe epilepsy. In connection with epilepsy and the treatment of seizures, the modulators of IL-1R AcP may reduce the severity and number of recurring seizures, and reduce the severity of the deleterious effects of seizures. The therapeutic modulators are also useful for reducing neuronal loss, neuronal degeneration, and gliosis associated with seizures.

Further, consistent with its presence in brain and CNS tissue, modulators of IL-1R AcP described herein are useful for treating critical illness polyneuropathy and myopathy (CIPNM) acute polyneuropathy; anorexia nervosa; Bell's palsy; chronic fatigue syndrome; transmissible dementia, including Creutzfeld-Jacob disease; demyelinating neuropathy; Guillain-Barre syndrome; vertebral disc disease; Gulf war syndrome; chronic inflammatory demyelinating polyneuropathy, myasthenia gravis; silent cerebral ischemia; sleep disorders, including narcolepsy and sleep apnea; chronic neuronal degeneration; and stroke, including cerebral ischemic diseases.

Rheumatic disorders that are treatable with the polypeptides of this invention include adult and juvenile rheumatoid arthritis; scleroderma; systemic lupus erythematosus; gout; osteoarthritis; polymyalgia rheumatica; seronegative spondylarthropathies, including ankylosing spondylitis, and Reiter's disease, psoriatic arthritis and chronic Lyme arthritis. Also treatable or preventable with these polypeptides are Still's disease and uveitis associated with rheumatoid arthritis. In addition, the polypeptide therapies of the invention are used in treating disorders resulting in inflammation of the voluntary muscle and other muscles, including dermatomyositis, inclusion body myositis, polymyositis, and lymphangioleimyomatosis.

The methods described herein can be treated with the polypeptides and inhibitors of this invention in combination with other cytokines, cytokine inhibitors and reagents. For example, IL-18 antagonists; including soluble IL-18 receptor, antibodies to IL-18 or the IL-18 receptor, IL-18 binding protein; TNF inhibitors, including ENBREL®; IL-1 inhibitors, including soluble forms of type II IL-1R, type II IL-1R, antibodies to IL-1, antibodies to type I IL-1R; and or other active agents that are effective in treating the disclosed medical conditions and diseases.

Polypeptides can be introduced into the extracellular environment by well-known means, such as by administering the protein intravenously or coupling it to a monoclonal antibody targeted to a specific cell type, to thereby affect signaling. When used as a therapeutic agent, polypeptides of the invention can be formulated into pharmaceutical compositions according to known methods. The polypeptides can be combined in admixture, either as the sole active material or with other known active materials, with pharmaceutically suitable diluents (e.g., Tris-HCl, acetate, phosphate), preservatives (e.g., Thimerosal, benzyl alcohol, parabens), emulsifiers, solubilizers, adjuvants and/or carriers. Suitable carriers and their formulations are described in Remington's Pharmaceutical Sciences, 16th ed. 1980, Mack Publishing Co. In addition, such compositions can contain the polypeptides complexed with polyethylene glycol (PEG), metal ions, or incorporated into polymeric compounds such as polyacetic acid, polyglycolic acid, hydrogels, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance of polypeptides of the invention.

The dosage of the composition can be readily determined by those of ordinary skill in the art. The amount to be administered and the frequency of administration can be determined empirically and will take into consideration the age and size of the patient being treated, as well as the malady being treated.

Treatment comprises administering the composition by any method familiar to those of ordinary skill in the art, including intravenous, intraperitoneal, intracorporeal injection, intra-articular, intraventricular, intrathecal, intramuscular, subcutaneous, topically, tonsillar, intranasally, intravaginally, and orally. The composition may also be given locally, such as by injection into the particular area, either intramuscularly or subcutaneously.

The polypeptides described herein can also be used for structure-based design of IL-1 inhibitors, or IL-1 receptor family member inhibitors or inhibitors of IL-1R AcP function. Such structure-based design is also known as "rational drug design." Polypeptides of this invention can be three dimensionally analyzed by, for example, X-ray crystallography, nuclear magnetic resonance, or homology modeling, all of which are well known methods. The use of structural information in molecular modeling software systems to assist in inhibitor design and inhibitor-interaction is also encompassed by the invention. Such computer-assisted modeling and drug design may utilize information such as chemical conformational analysis, electrostatic potential of the molecules, protein folding, etc. For example, most of the design of class-specific inhibitors of metalloproteases has focused on attempts to chelate or bind the catalytic zinc atom. Synthetic inhibitors are usually designed to contain a negatively charged moiety to which is attached a series of other groups designed to fit the specificity pockets of the particular protease. A particular method of the invention comprises analyzing the three dimensional structure of the IL-1R AcP of this invention for likely binding sites of substrates, synthesizing a new molecule that incorporates a predictive reactive site, and assaying the new molecule as described above.

The polynucleotides and polypeptides of this invention, and antibodies against the polypeptides described herein can be used as reagents in a variety of research protocols. A sample of such research protocols are given in Sambrook et al. *Molecular Cloning: A Laboratory Manual*, 2 ed. Vol. 1-3, Cold Spring Harbor Laboratory Press, (1989). For example, these reagents can serve as markers for cell specific or tissue specific expression of RNA or proteins. Similarly, these reagents can be used to investigate constituitive and transient expression of IL-1R AcP splice variant RNA or polypeptides.

Antibodies that are immunoreactive with the polypeptides of the invention are provided herein. Such antibodies specifically bind to the polypeptides via the antigen-binding sites of the antibody (as opposed to non-specific binding). Thus, the polypeptides, fragments, variants, fusion proteins, etc., as set forth above may be employed as immunogens in producing antibodies immunoreactive therewith.

The IL-1R AcP splice variant, fragments of the splice variant, the cytoplasmic domain, fragments of the cytomplasmic domain, amino acids 379-687, amino acids 384-687, and amino acids 449-687, all of SEQ ID NO:2 and amino acids 449-685, amino acids 379-687, amino acids 389-687, all of SEQ ID NO:4 can be utilized to prepare antibodies that specifically bind to IL-1R AcP. The term "antibodies" is meant to include polyclonal antibodies, monoclonal antibodies, fragments thereof, such as F(ab')2 and Fab fragments, as well as any recombinantly produced binding partners. Antibodies are defined to be specifically binding if they bind the IL-1R AcP polypeptide with a $K_a$ of greater than or equal to about $10^7$ $M^{-1}$. Affinities of binding partners or antibodies can be readily determined using conventional techniques, for example those described by Scatchard et al., *Ann. N.Y. Acad. Sci.*, 51:660 (1949).

Polyclonal antibodies can be readily generated from a variety of sources, for example, horses, cows, goats, sheep, dogs, chickens, rabbits, mice, or rats, using procedures that are well known in the art. In general, purified peptide that is appropriately conjugated is administered to the host animal typically through parenteral injection. The immunogenicity of the polypeptide can be enhanced through the use of an adjuvant, for example, Freund's complete or incomplete adjuvant. Following booster immunizations, small samples of serum are collected and tested for reactivity to the polypeptide. Examples of various assays useful for such determination include those described in *Antibodies: A Laboratory Manual*, Harlow and Lane (eds.), Cold Spring Harbor Laboratory Press, 1988; as well as procedures, such as countercurrent immuno-electrophoresis (CIEP), radioimmunoassay, radio-immunoprecipitation, enzyme-linked immunosorbent assays (ELISA), dot blot assays, and sandwich assays. See U.S. Pat. Nos. 4,376,110 and 4,486,530.

Monoclonal antibodies can be readily prepared using well known procedures. See, for example, the procedures described in U.S. Pat. Nos. RE 32,011, 4,902,614, 4,543,439, and 4,411,993; Monoclonal Antibodies, Hybridomas: *A New Dimension in Biological Analyses*, Plenum Press, Kennett, McKearn, and Bechtol (eds.), 1980. Briefly, the host animals, such as mice, are injected intraperitoneally at least once and preferably at least twice at about 3 week intervals with isolated and purified peptide, optionally in the presence of adjuvant. Mouse sera are then assayed by conventional dot blot technique or antibody capture (ABC) to determine which animal is best to fuse. Approximately two to three weeks later, the mice are given an intravenous boost of peptide. Mice are later sacrificed and spleen cells fused with commercially available myeloma cells, such as Ag8.653 (ATCC), following established protocols. Briefly, the myeloma cells are washed several times in media and fused to mouse spleen cells at a ratio of about three spleen cells to one myeloma cell. The fusing agent can be any suitable agent used in the art, for example, polyethylene glycol (PEG). Fusion is plated out into plates containing media that allows for the selective growth of the fused cells. The fused cells can then be allowed to grow for approximately eight days. Supernatants from resultant hybridomas are collected and added to a plate that is first coated with goat anti-mouse Ig. Following washes, a label, such as $^{125}$I-IL-1R AcP, is added to each well followed by incubation. Positive wells can be subsequently detected by autoradiography. Positive clones can be grown in bulk culture and supernatants are subsequently purified over a Protein A column (Pharmacia).

The monoclonal antibodies of the invention can be produced using alternative techniques, such as those described by Alting-Mees et al., "Monoclonal Antibody Expression Libraries: A Rapid Alternative to Hybridomas", *Strategies in Molecular Biology* 3:1-9 (1990), which is incorporated herein by reference. Similarly, binding partners can be constructed using recombinant DNA techniques to incorporate the variable regions of a gene that encodes a specific binding antibody. Such a technique is described in Larrick et al., *Biotechnology*, 7:394 (1989).

Antigen-binding fragments of such antibodies, which may be produced by conventional techniques, are also encompassed by the present invention. Examples of such fragments include, but are not limited to, Fab and F(ab')$_2$ fragments. Antibody fragments and derivatives produced by genetic engineering techniques are also provided.

The monoclonal antibodies of the present invention include chimeric antibodies, e.g., humanized versions of murine monoclonal antibodies. Such humanized antibodies may be prepared by known techniques, and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332:323, 1988), Liu et al. (*PNAS* 84:3439, 1987), Larrick et al. (*Bio/Technology* 7:934, 1989), and Winter and Harris (*TIPS* 14:139, May, 1993). Procedures to generate antibodies transgenically can be found in GB 2,272,440, U.S. Pat. Nos. 5,569,825 and 5,545,806 and related patents claiming priority therefrom, all of which are incorporated by reference herein.

In one embodiment, the antibodies are specific for the polypeptides of the present invention, and do not cross-react with other proteins. Screening procedures by which such antibodies may be identified are well known, and may involve immunoaffinity chromatography, for example.

Hybridoma cell lines that produce monoclonal antibodies specific for the polypeptides of the invention are also contemplated herein. Such hybridomas may be produced and identified by conventional techniques. One method for producing such a hybridoma cell line comprises immunizing an animal with a polypeptide; harvesting spleen cells from the immunized animal; fusing said spleen cells to a myeloma cell line, thereby generating hybridoma cells; and identifying a hybridoma cell line that produces a monoclonal antibody that binds the polypeptide. The monoclonal antibodies may be recovered by conventional techniques.

Antibodies that are immunoreactive with the polypeptides of the invention are provided herein. Such antibodies specifically bind to the polypeptides via the antigen-binding sites of the antibody (as opposed to non-specific binding). Thus, the polypeptides, fragments, variants, fusion proteins, etc., as set forth above may be employed as "immunogens" in producing antibodies immunoreactive therewith. More specifically, the polypeptides, fragment, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, *Immuno Biology* 3:9 (Garland Publishing Inc., 2nd ed. 1996)). Because folded proteins have complex surfaces, the number of epitopes available is quite numerous; however, due to the conformation of the protein and steric hinderances, the number of antibodies that actually bind to the epitopes is less than the number of available epitopes (C. A. Janeway, Jr. and P. Travers, *Immuno Biology* 2:14 (Garland Publishing Inc., 2nd ed. 1996)). Epitopes may be identified by any of the methods known in the art.

Thus, one aspect of the present invention relates to the antigenic epitopes of the polypeptides of the invention. Such epitopes are useful for raising antibodies, in particular monoclonal antibodies, as described in more detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides of the invention, whether the epitopes have been isolated or remain part of the polypeptides, both polyclonal and monoclonal antibodies may be prepared by conventional techniques. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988).

Those antibodies that additionally can block binding of the polypeptides of the invention to IL-1 or IL-1 receptor family members may be used to inhibit a biological activity that results from such binding. For example, activation of the transcription factors NFκB and AP1, the protein kinases Jun N-terminal kinase and p38 map, the enzymes COX-2 leading to prostaglandin production and iNOS leading to nitric oxide production, and inflammation in general may be inhibited.

Such an antibody may be employed in an in vitro procedure, or administered in vivo to inhibit a biological activity mediated by the entity that generated the antibody. Disorders caused or exacerbated (directly or indirectly) by the interaction of IL-1 with cell surface (binding partner) receptor thus may be treated. A therapeutic method involves in vivo administration of a blocking antibody to a mammal in an amount effective in inhibiting a IL-1-mediated biological activity. Monoclonal antibodies are generally preferred for use in such therapeutic methods. In one embodiment, an antigen-binding antibody fragment is employed.

Antibodies may be screened for agonistic (i.e., ligand-mimicking) properties. Such antibodies, upon binding to cell surface IL-1R AcP polypeptides, induce biological effects (e.g., transduction of biological signals) similar to the biological effects induced when IL-1R AcP of this invention mediates its effects by interacting with IL-1 receptor family members. Agonistic antibodies may be used to induce the ability of IL-1R AcP polypeptides to promote cell signaling leading to activation of the transcription factors NFκB and AP1 (Stylianou et al., *Int. J. Biocem Cell Biol*. 30: 1075-1079, 1998), the protein kinases Jun N-terminal kinase and p38 map kinase (O'Neil et al., J. Leuokoc. Biol. 63:650-657, 1998), the enzymes COX-2 leading to prostaglandin production (Crofford, *J. Rheumatol*. 24 Suppl. 49:15-19, 1997) and iNOS leading to nitric oxide production (Alexander, *Nutrition* 14: 376-90) and inflammation in general.

Also provided herein are conjugates comprising a detectable (e.g., diagnostic) or therapeutic agent, attached to the antibody. Examples of such agents are presented above. The conjugates find use in in vitro or in vivo procedures.

The references cited herein are incorporated by reference herein in their entirety.

EXAMPLE 1

IL-1R AcP of This Invention Can Inhibit NF-κB Signaling and Is Primarily Expressed in Brain The following are results of experiments designed to determine expression patterns of the IL-1R AcP of this invention. Table I shows the results of expression data and compares the results with the IL-1R AcP described in WO 96/23067. Expression is limited to brain/CNS tissue. The data in Table I is RT-PCR data from cDNAs from human brain tissues. The data in FIG. 1 describe expression in tissues as compared to a control. This data is from a Taqman analysis of RNA expression. The data shown in FIG. 1 and Table I support the conclusion that expression of the IL-1R AcP of this invention is expressed largely in brain/CNS tissue.

In in vitro experiments, in response to IL-1R, IL-1R AcP of this invention that is overexpressed in COS7 cells does not activate NF-κB and inhibits normal NF-κB signaling. Thus, in certain situations, in particular when overexpressed in vitro, IL-1R AcP of this invention acts to antagonize cellular responses to IL-1.

TABLE I

| BRAIN TISSUE | IL-1R | IL-1R AcP of WO 96/23067 | IL-1R AcP of this invention |
|---|---|---|---|
| Total Brain | ++ | ++ | ++ |
| Fetal brain | ++ | ++ | ++ |
| Frontal lobe | ++ | + | ++ |
| Temporal lobe | ++ | ++ | ++ |
| Occipital lobe | ++ | ++ | ++ |
| Parietal lobe | ++ | ++ | ++ |
| Cerebral cortex | ++ | ++ | ++ |
| Pons | ++ | ++ | ++ |
| Cerebellum | ++ | ++ | ++ |
| Medulla Oblongata | ++ | ++ | ++ |
| Hippocampus | ++ | ++ | ++ |
| Amygdala | * | ++ | ++ |
| Thalamus | ++ | ++ | ++ |
| *Corpus Callosum* | + | -- | ++ |
| Cerebral | ++ | ++ | ++ |
| Peduncles | | | |
| Spinal cord | ++ | ++ | ++ |
| Substantia nigra | ++ | ++ | ++ |

The embodiments within the specification provide an illustration of embodiments of the invention and should not be construed to limit the scope of the invention. The skilled artisan recognizes many other embodiments are encompassed by the claimed invention.

What is claimed is:

1. An isolated polypeptide selected from the group consisting of:
   a) A polypeptide comprising SEQ ID NO:2, wherein the amino acid at 598 is Thr or Pro;
   b) A polypeptide comprising amino acids 449-687 of SEQ ID NO:2, wherein the amino acid at 598 is Thr or Pro;
   c) A polypeptide comprising amino acids 384-687 of SEQ ID NO:2, wherein the amino acid at 598 is Thr or Pro; and
   d) A polypeptide comprising amino acids 379-687 of SEQ ID NO:2, wherein the amino acid at 598 is Thr or Pro.

2. An isolated polypeptide consisting of at least 20 or at least 30 contiguous amino acids of the polypeptide of SEQ ID NO:2, wherein the polypeptide can be used to prepare an antibody that specifically binds to amino acids 449-687 of SEQ ID NO:2 wherein the amino acid at 598 is Thr or Pro.

* * * * *

UNITED STATES PATENT AND TRADEMARK OFFICE
CERTIFICATE OF CORRECTION

| | |
|---|---|
| PATENT NO. | : 7,285,634 B2 |
| APPLICATION NO. | : 11/387672 |
| DATED | : October 23, 2007 |
| INVENTOR(S) | : Sims et al. |

It is certified that error appears in the above-identified patent and that said Letters Patent is hereby corrected as shown below:

On the title page item (56) References Cited; under FOREIGN PATENT DOCUMENTS: change "WO97 23067" to -- WO 96/23067 --

Signed and Sealed this

Thirty-first Day of March, 2009

JOHN DOLL
*Acting Director of the United States Patent and Trademark Office*